United States Patent

Hofmeister et al.

(10) Patent No.: US 6,703,405 B2
(45) Date of Patent: Mar. 9, 2004

(54) SUBSTITUTED 4-PHENYLTETRAHYDROISOQUINOLINIUM SALTS, PROCESS FOR THEIR PREPARATION, THEIR USE AS A MEDICAMENT, AND MEDICAMENT CONTAINING THEM

(75) Inventors: Armin Hofmeister, Oppenheim (DE); Hans-Jochen Lang, Hofheim (DE); Uwe Heinelt, Wiesbaden (DE); Markus Bleich, Hünfelden-Dauborn (DE); Klaus Wirth, Kriftel (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/324,041

(22) Filed: Dec. 20, 2002

(65) Prior Publication Data

US 2003/0171580 A1 Sep. 11, 2003

Related U.S. Application Data

(60) Provisional application No. 60/353,614, filed on Feb. 1, 2002.

(30) Foreign Application Priority Data

Dec. 22, 2001 (DE) .......................................... 101 63 914

(51) Int. Cl.$^7$ ........................ C07D 217/10; A61K 31/47

(52) U.S. Cl. ...................................... 514/307; 546/139

(58) Field of Search ........................... 546/139; 514/307

(56) References Cited

U.S. PATENT DOCUMENTS

| | | | |
|---|---|---|---|
| 3,666,763 A | 5/1972 | Grethe et al. | 260/289 |
| 5,547,953 A | 8/1996 | Weichert et al. | 514/307 |

FOREIGN PATENT DOCUMENTS

| | | |
|---|---|---|
| CA | 2406161 | 10/2002 |
| DE | 100 19 062 | 10/2001 |
| EP | 0 659 748 | 6/1995 |
| EP | 1 113 007 A1 | 7/2001 |
| WO | WO01/32624 A1 | 5/2001 |
| WO | WO01/32625 A1 | 5/2001 |

OTHER PUBLICATIONS

Kihara et al, Journal of Medicinal Chem, Vol 33, No. 8, 1990, pp. 2283–2286.*
Dandridge et al, Journal of Medicinal Chem, Vol 27, No. 1, pp. 28–35.*
Eiden et al, Chemical Abstracts, Vol 87, No. 13, Abstract 102,137p, Sep. 27, 1977, p. 602.*
W.R. Meindl et al., "Benzylamines: Synthesis and Evaluation of Antimycobacterial Properties", J. Med. Chem., vol. 27, pp. 1111–1118, (1984).
D. Ben–Ishai et al, "Intra vs. Intermolecular Amidoalkylation of Aromatics", Tetrahedron, vol. 43, No. 2, pp. 439–450, (1987).
D.L. Trepanier et al., "3,4–Dihydroiisocarbostyril and 1,2, 3,4–Tetrahydroisoquinoline Derivatives of Ephedrine", Journal of Medicinal Chemistry, vol. 16, No. 4, pp. 342–347, (1973).
S. Kano et al., "A Synthesis of Simple 4,4–Disubstituted Tetrahydroisoquinolines by Cyclization of α, α–Disubstituted Phenylacetamides", Chem. Pharm. Bull., vol. 33, No. 1, pp. 340–346, (1985).
Z. Zhao et al., "A Practical Synthesis of 4–(3',4'–Dihydroxylphenyl)–1,2,3,4–Tetrahydroisoquinoline", OPPI Briefs, vol. 27, No. 4, pp. 513–516, (1995).
J.C. Cuevas et al., "α–Silylated Tertiary Benzamides as Dual Ortho–and α–Carbanion Synthons. Carbodesilylative Routes to Isoquinoline and Dibenzoquinolizidine Derivatives", Tetrahedron Letters, vol. 30, No. 43, pp. 5837–5840, (1989).
M. Kihara et al. "Synthesis and Enantioselectivity of Optically Active 1–and 3–Substituted 4–Phenyl–1, 2,3, 4–Tetrahydroisoquinolin–4–OLS and Related Compounds as Norepinephrine Potentiators", Chem. Pharm. Bull., vol. 43, No. 9, pp. 1543–1546, (1995).

* cited by examiner

Primary Examiner—Zinna Northington Davis
(74) Attorney, Agent, or Firm—Finnegan, Henderson, Farabow, Garrett, & Dunner, L.L.P.

(57) ABSTRACT

The invention relates to novel compounds of the formula I

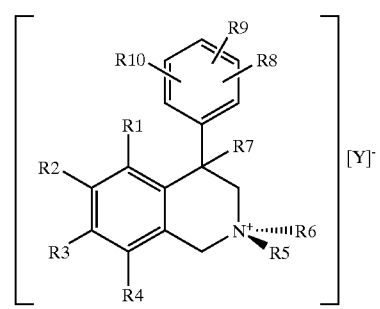

in which R1 to R10 R7 are as defined herein. In one embodiment, these compounds may be used as antihypertensives, for reducing or preventing ischemia-induced damage, as medicaments for surgical intervention for the treatment of ischemias of the nervous system, of stroke and of cerebral edema, of shock, of impaired respiratory drive, for the treatment of snoring, as laxative, as agent against ectoparasites, to prevent the formation of gallstones, as antiatherosclerotics, agents against late complications of diabetes, cancers, fibrotic disorders, endothelial dysfunction, organ hypertrophies and hyperplasias. In another embodiment, the compounds may be inhibitors of the cellular sodium-proton antiporter and influence serum lipoproteins and thus be used for the treatment of atherosclerotic lesions.

23 Claims, No Drawings

SUBSTITUTED 4-PHENYLTETRAHYDROISOQUINOLINIUM SALTS, PROCESS FOR THEIR PREPARATION, THEIR USE AS A MEDICAMENT, AND MEDICAMENT CONTAINING THEM

This application claims the benefit of foreign priority under 35 U.S.C. §119 of German patent application no. 10163914.7, filed on Dec. 22, 2001 and the contents of which are incorporated by reference herein. This application also claims the benefit of priority of U.S. Provisional Application No. 60/353,614, filed Feb. 1, 2002, the contents of which are incorporated by reference herein.

DESCRIPTION

Substituted 4-phenyltetrahydroisoquinolinium salts, process for their preparation, their use as medicament, and medicament containing them The invention relates to compounds of the formula I

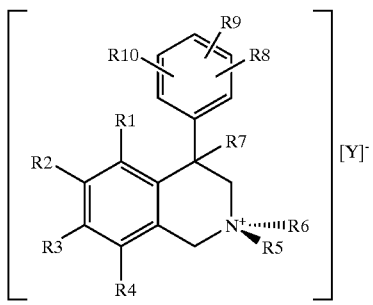

wherein
R1, R2, R3 and R4 are independently of one another H, F, Cl, Br, I, CN, $NO_2$, OH, $NH_2$, $C_aH_{2a+1}$, $C_{qq}H_{2qq-1}$, $OC_bH_{2b+1}$, COOR50, OCOR50, COR50 or $O_x$—$(CH_2)_y$— phenyl; wherein
a and b are independently of one another 1, 2, 3, 4, 5, 6, 7 or 8, wherein the groups $C_aH_{2a+1}$ and $OC_bH_{2b+1}$ independently of one another are unsubstituted or substituted where one or more H atoms are replaced by F atoms;
qq is 3, 4, 5, 6, 7 or 8, wherein the group $C_{qq}H_{2qq-1}$ is unsubstituted or substituted where one or more H atoms are replaced by F atoms;
R50 is H or $C_cH_{2c+1}$,
c is 1, 2, 3, 4, 5, 6, 7 or 8, wherein the group $C_cH_{2c+1}$ is unsubstituted or substituted where one or more H atoms are replaced by F atoms;
x is zero or 1;
y is zero, 1, 2, 3 or 4, where the phenyl ring in the group $O_x$—$(CH_2)_y$— phenyl is unsubstituted or substituted by 1–3 independently chosen from F, Cl, Br, CN, $NO_2$, OH, $NH_2$ and $C_dH_{2d+1}$,
d is 1, 2, 3 or 4, wherein the group $C_dH_{2d+1}$ is unsubstituted or substituted where one or more H atoms are replaced by F atoms; or
R1, R2, R3 and R4 are independently of one another chosen from a heteroaryl with at least one heteroatom chosen from 1, 2, 3 or 4 N atoms, 1 oxygen atom and 1 S atom, present as ring atoms; or
R1, R2, R3 and R4 are independently of one another CONR11R12 or NR11R12;

wherein
R11 and R12 are independently of one another H, $C_eH_{2e+1}$, or $C_{rr}H_{2rr-1}$,
e is 1, 2, 3, 4, 5, 6, 7 or 8;
rr is 3, 4, 5, 6, 7, or 8, wherein the groups $C_eH_{2e+1}$ and $C_{rr}H_{2rr-1}$ independently of one another are unsubstituted or substituted where one or more H atoms are replaced by F atoms and/or one or more $CH_2$ groups are replaced by O or NR13;
R13 is H or $C_fH_{2f+1}$;
f is 1, 2, 3 or 4, wherein the group $C_fH_{2f+1}$ is unsubsitituted or substituted where one or more H atoms are replaced by F atoms; or
R13 and a $CH_2$ group of R11 or R12 together with the N atom to which they are bonded form a 5- or 6-membered ring; or
R11 and R12 together with the N atom to which they are bonded form a 5-, 6- or 7-membered ring; or
R11 and R12 are independently of one another COR14, CSR14 or $SO_2$R14; wherein
R14 is $C_gH_{2g+1}$;
g is 1, 2, 3, 4, 5, 6, 7 or 8, wherein the group $C_gH_{2g+1}$ is unsubsitituted or substituted where one or more H atoms are replaced by F atoms, and/or one or more $CH_2$ groups are replaced by O or NR13; or
R1, R2, R3 and R4 are independently of one another —$O_h$—$SO_j$—R15; wherein
h is zero or 1;
j is zero, 1 or 2;
R15 is $C_kH_{2k+1}$, OH, $OC_lH_{2l+1}$ or NR17R18;
k is 1, 2, 3, 4, 5, 6, 7 or 8, wherein the group $C_kH_{2k+1}$ is unsubsitituted or substituted where one or more H atoms are replaced by F atoms;
l is 1, 2, 3, 4, 5, 6, 7 or 8, wherein the group $OC_lH_{2l+1}$ is unsubsitituted or substituted where one or more H atoms are replaced by F atoms;
R17 and R18 are independently of one another H or $C_mH_{2m+1}$;
m is 1, 2, 3, 4, 5, 6, 7 or 8, wherein the group $C_mH_{2m+1}$ is unsubstituted or substituted where one or more H atoms is replaced by F atoms and/or one or more $CH_2$ groups are replaced by O, CO, CS or NR19;
R19 is H or $C_nH_{2n+1}$;
n is 1, 2, 3 or 4, wherein the group $C_nH_{2n+1}$ is unsubstituted or substituted where one or more H atoms are replaced by F atoms; or
R17 and R18 together with the N atom to which they are bonded form a 5-, 6- or 7-membered ring; or
R19 and a $CH_2$ group of R17 or R18 together with the N atom to which they are bonded form a 5- or 6-membered ring;
R5 and R6 are independently of one another $C_pH_{2p+1}$, $C_{ss}H_{2ss-1}$, COR20 or $SO_2$R20; wherein
p is 1, 2, 3, 4, 5, 6, 7 or 8;
ss is 3, 4, 5, 6, 7 or 8;
R20 is $C_qH_{2q+1}$;
q is 1, 2, 3, 4, 5, 6, 7 or 8, wherein the groups $C_pH_{2p+1}$, $C_{ss}H_{2ss-1}$ and $C_qH_{2q+1}$ independently of one another are unsubstituted or substituted where one or more H atoms are replaced by F atoms and/or one or more $CH_2$ groups are replaced by O or NR21;
R21 is H or $C_rH_{2r+1}$;
r is 1, 2, 3 or 4; wherein the group $C_rH_{2r+1}$ is unsubstituted or substituted where one or more H atoms are replaced by F atoms;

R7 is H, F, Cl, Br, I, $C_sH_{2s+1}$, $C_{dd}H_{2dd-1}$, OH, $OC_tH_{2t+1}$ or OCOR22; wherein s and t are independently of one another 1, 2, 3, 4, 5, 6, 7 or 8;
  dd is 3, 4, 5, 6, 7 or 8, wherein the groups $C_sH_{2s+1}$, $C_{dd}H_{2dd-1}$ and $OC_tH_{2t+1}$ independently of one another are unsubstituted or substituted where one or more H atoms are replaced by F atoms;

R22 is $C_uH_{2u+1}$;
  u 1, 2, 3 or 4, wherein the group $C_uH_{2u+1}$ is unsubstituted or substituted where one or more H atoms are replaced by F atoms;

R8, R9 and R10 are independently of one another —$O_v$—$SO_w$—$R^{23}$; wherein
  v is zero or 1;
  w is zero, 1 or 2;

R23 is $C_{nn}H_{2nn+1}$, $C_{mm}H_{2mm-1}$, OH, $OC_{pp}H_{2pp+1}$ or NR25R26; nn and pp are independently of one another 1, 2, 3, 4, 5, 6, 7 or 8, mm is 3, 4, 5, 6, 7 or 8, wherein the groups $C_{nn}H_{2nn+1}$, $C_{mm}H_{2mm-1}$ and $OC_{pp}H_{2pp+1}$ independently of one another are unsubstituted or substituted where one or more H atoms are replaced by F atoms;

R25 and R26 are independently of one another H, CN, $C_zH_{2z+1}$, or $C_{zz}H_{2zz-1}$;
  z is 1, 2, 3, 4, 5, 6, 7 or 8;
  zz is 3, 4, 5, 6, 7 or 8, wherein the group $C_zH_{2z+1}$ is unsubstituted or substituted where one or more H atoms are replaced by F atoms and,
  wherein the group $C_zH_{2z+1}$, is unsubstituted or substituted where one or more H atoms are replaced by F atoms and/or one or more $CH_2$ groups are replaced by O, CO, CS or NR27;

R27 is H or $C_{aa}H_{2aa+1}$;
  aa is 1, 2, 3 or 4, wherein the group $C_{aa}H_{2aa+1}$ is unsubstituted or substituted where one or more H atoms are replaced by F atoms; or
R27 and a $CH_2$ group of R25 or R26 together with the N atom to which they are bonded form a 5- or 6-membered ring; or
R25 and R26 together with the N atom to which they are bonded form a 5-, 6- or 7-membered ring, or
R8, R9 and R10 are independently of one another NR32COR30, NR32CSR30 or $NR32SO_{bb}R30$; wherein
  R30 is H, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;
  R32 and R33 are independently of one another H or $C_hH_{2h+1}$;
  bb is 2 or 3;
  cc is 1, 2, 3, 4, 5, 6, 7 or 8;
  yy is 3, 4, 5, 6, 7 or 8;
  h is 1, 2, 3, 4, 5, 6, 7 or 8,
    wherein the group $C_hH_{2h+1}$ is unsubstituted or substituted where one or more H atoms are replaced by F atoms, and wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups are replaced by O or NR31;
R31 is H, $C_{kk}H_{2kk+1}$, or COR65;
  kk is 1, 2, 3, or 4; wherein the group $C_{kk}H_{2kk+1}$ is unsubstituted or substituted where one or more H atoms are replaced by F atoms, R65 is H, or $C_{xx}H_{2xx+1}$;

xx is 1, 2, 3 or 4, wherein the group $C_{xx}H_{2xx+1}$ is unsubstituted or substituted where one or more H atoms are replaced by F atoms; or
R31 together with a $CH_2$ group of R30 and the N atom to which they are jointly bonded forms a 5-, 6- or 7-membered ring; or
R30 is a 5- or 6-membered heteroaryl with at least one hetero atom chosen from 1, 2, 3 or 4 N atoms, 1 S atoms and 1 O atoms which is unsubstituted or substituted by up to three substituents chosen from F, Cl, Br, I, $C_{oo}H_{2oo+1}$, and NR70R71;
R70 and R71 are independently of one another H, $C_{uu}H_{2uu+1}$ or COR72;
R72 is H, or $C_{vv}H_{2vv+1}$;
  oo, uu and vv are independently of one another 1, 2, 3, 4, 5, 6, 7 or 8, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms; or
R8, R9 and R10 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 OCOR42;
  ee and ff are independently of one another 1, 2, 3, 4, 5, 6, 7 or 8;
  ww is 3, 4, 5, 6, 7 or 8, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;
R40 and R41 are independently of one another H or $C_{tt}H_{2tt+1}$;
  tt is 1, 2, 3, 4, 5, 6, 7 or 8, wherein the group $C_{tt}H_{2tt+1}$ is unsubstituted or substituted where one or more H atoms are replaced by F atoms and/or where one or more $CH_2$ groups are replaced by O or NR44;
R44 is H or $C_{gg}H_{2gg+1}$;
  gg is 1, 2, 3, 4, 5, 6, 7 or 8, wherein the group $C_{gg}H_{2gg+1}$ is unnsubstituted or substituted where one or more H atoms are replaced by F atoms; or
R40 and R41 with the N atom to which they are bonded for a 5- or 6-membered ring;
R42 is H or $C_{hh}H_{2hh+1}$;
  hh is 1, 2, 3, 4, 5, 6, 7 or 8, wherein the group $C_{hh}H_{2hh+1}$ is unnsubstituted or substituted where one or more H atoms are replaced by F atoms;
Y is chosen from fluorine, chlorine, bromine, iodine, hydroxyl and all anionic forms of pharmacologically acceptable mono-, di- or tricarboxylic acids and sulfonic acids;
and their pharmaceutically acceptable salts, and the trifluoroacetic acid salts.

In another embodiment, compounds of the formula 1 are chosen from:

R1, R2, R3 and R4 are independently of one another, H, F, Cl, Br, I, CN, $NO_2$, OH,
$NH_2$, $C_aH_{2a+1}$, cycloalkyl with 3, 4, 5 or 6 C atoms, $OC_bH_{2b+1}$, or COOR50; wherein a and b are independently of one another 1, 2, 3 or 4, wherein the group $C_aH_{2a+1}$ is unsubstituted or substituted where one or more H atoms are replaced by F atoms;
R50 is H or $C_cH_{2c+1}$;
  c is 1, 2, 3 or 4, wherein the group $C_cH_{2c+1}$ is unsubstituted or substituted where one or more H atoms are replaced by F atoms;
or R1, R2, R3 and R4 are independently of one another a 5- or 6-membered heteroaryl chosen from imidazolyl, pyrazolyl, pyrrolyl, triazolyl, tetrazolyl, thiazolyl and oxazolyl; or R1, R2, R3 and R4 are independently of one another CONR11R12 or NR11R12; wherein
  R11 and R12 are independently of one another H, $C_eH_{2e+1}$, or $C_{rr}H_{2rr-1}$;
    e is 1, 2, 3 or 4;
    rr is 3, 4, 5 or 6, wherein the groups $C_eH_{2e+1}$ and $C_{rr}H_{2rr-1}$ independently of one another are unsubstituted or substituted where one or more H atoms are replaced by F atoms; or
  R11 and R12 independently of one another are hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or
  R11 and R12 together with the N atom to which they are bonded form a pyrrolidine, piperidine, N-methylpiperazine, piperazine or morpholine ring; or
  R11 and R12 are independently of one another COR14, CSR14, CONHR14, CSNHR14 or $SO_2R14$; wherein
  R14 is $C_gH_{2g+1}$;
    g is 1, 2, 3 or 4, wherein the group $C_gH_{2g+1}$ is unsubstituted or substituted where one or more H atoms are replaced by F atoms; or
R1, R2, R3 and R4 are independently of one another $OSO_3H$, $SO_3H$, $SO_2R_{15}$; wherein
  R15 is $C_kH_{2k+1}$, $OC_lH_{2l+1}$ or NR17R18;
    k 1, 2, 3 or 4, wherein the group $C_kH_{2k+1}$ is unsubstituted or substituted where one ore more H atoms are replaced by F atoms;
    l 1, 2, 3 or 4, wherein the group $OC_lH_{2l+1}$ is unsubstituted or substituted where one ore more H atoms are replaced by F atoms;
  R17 and R18 are independently of one another H, $C_mH_{2m+1}$ or $C_mH_{2m+1}$, in which a first $CH_2$ group bonded to the nitrogen of NR17R18 is replaced by CO and a second $CH_2$ group is replaced by NR19;
    m 1, 2, 3, 4 or 5, wherein the group $C_mH_{2m+1}$ is unsubstituted or substituted where one or more H atoms is replaced by F atoms;
    R19 is H or $C_nH_{2n+1}$;
    n is 1, 2, 3 or 4, wherein the group $C_nH_{2n+1}$ is unsubstituted or substituted where one or more H atoms is replaced by F atoms; or
  R17 and R18 together with the N atom to which they are bonded a 5- or 6-membered ring;
R5 and R6 are independently of one another $C_pH_{2p+1}$;
  p is 1, 2, 3 or 4, wherein the group $C_pH_{2p+1}$ is unsubstituted or substituted where one or more H atoms is replaced by F atoms;
R7 is H, $C_sH_{2s+1}$, $OC_tH_{2t+1}$ or OCOR22; wherein s and t are independently of one another 1, 2, 3 or 4, wherein the groups $C_sH_{2s+1}$ and $OC_tH_{2t+1}$ independently of another are unsubstituted or substituted where one or more H atoms is replaced by F atoms;
  R22 is $C_uH_{2u+1}$;
    u is 1, 2, 3 or 4; wherein the group $C_uH_{2u+1}$ is unsubstituted
    or substituted where one or more H atoms is replaced by F atoms;
R8, R9 and R10 are independently of one another $OSO_3H$, $SO_3H$ or $SO_2R23$; wherein
  R23 is $C_{nn}H_{2nn+1}$, $C_{mm}H_{2mm-1}$, $OC_{pp}H_{2pp+1}$ or NR25R26;
    nn and pp are independently of one another 1, 2, 3, 4 or 5,
    mm is 3, 4, 5 or 6, wherein the groups $C_{nn}H_{2nn+1}$, $C_{mm}H_{2mm-1}$ and $OC_{pp}H_{2pp+1}$ independently of another are unsubstituted or substituted where one or more H atoms is replaced by F atoms;
  R25 and R26 are independently of one another H, CN, $C_zH_{2z+1}$ or $C_zH_{2z+1}$, in which a first $CH_2$ group bonded to the nitrogen of NR25R26 is replaced by CO or CS and a second $CH_2$ is replaced by NR27;
    z is 1, 2, 3, 4, 5 or 6; wherein the group $C_zH_{2z+1}$ is unsubstituted or substituted where one or more H atoms are replaced by F atoms;
  R27 is H or $C_{aa}H_{2aa+1}$;
    aa is 1, 2, 3 or 4, wherein the group $C_{aa}H_{2aa+1}$ is unsubstituted or substituted where one or more H atoms are replaced by F atoms; or
  R27 and a $CH_2$ group of R25 or R26 together with the N atom to which they are bonded form a 5- or 6-membered ring; or
  R25 and R26 together with the N atom to which they are bonded form a 5- or 6-membered ring; or
R8, R9 and R10 are independently of one another NR32COR30, NR32CSR30 or $NR32SO_2R30$; wherein
  R30H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;
R32 and R33 are independently of one another H or $C_hH_{2h+1}$;
  cc is 1, 2, 3, 4, 5 or 6;
  yy is 3, 4, 5 or 6;
  h is 1, 2, 3 or 4; wherein the group $C_hH_{2h+1}$ is unsubstituted or substituted where one or more H atoms are replaced by F atoms, and wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups are replaced by O or NR31;
  R31 is H, $C_{kk}H_{2kk+1}$ or COR65;
    kk is 1, 2, 3, or 4, wherein the group $C_{kk}H_{2kk+1}$ is unsubstituted or substituted where one or more H atoms are replaced by F atoms,
  R65 is H or $C_{xx}H_{2xx+1}$;
    xx is 1, 2, 3 or 4, wherein the group $C_{xx}H_{2xx+1}$ is unsubstituted where one or more H atoms are replaced by F atoms; or
  R31 together with a $CH_2$ group of R30 and the N atom to which they are jointly bonded form a 5- or 6-membered ring; or
  R30 is a 5- or 6-membered heteroaryl chosen from pyridyl, imidazolyl, pyrazolyl, pyrrolyl, triazolyl, tetrazolyl, thienyl, thiazolyl and oxazolyl;
    which is unsubstituted or substituted by up to three substituents chosen from F, Cl, Br, I, $C_{oo}H_{2oo+1}$, and NR70R71,
  R70 and R71 are independently of one another H, $C_{uu}H_{2uu+1}$ or COR72;
  R72 is H or $C_{vv}H_{2vv+1}$;
    oo, uu and vv are independently of one another 1, 2, 3 or 4, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms; or
R8, R9 and R10 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 or OCOR42;
  ee and ff are independently of one another 1, 2, 3 or 4;

ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;

R40 and R41 are independently of one another H or $C_{tt}H_{2tt+1}$;

tt is 1, 2, 3, 4, 5, 6, 7 or 8, wherein the group $C_{tt}H_{2tt+1}$ is unsubstituted or substituted where one or more H atoms are replaced by F atoms; or R40 and R41 are independently of one another chosen from hydroxyethyl, N,N-dimethylaminoethyl, N,N-diethylaminoethyl, pyrrolidinoethyl, N-methylpiperazinoethyl, piperazinoethyl, morpholinoethyl and piperidinoethyl; or R40 and R41 together with the N atom to which they are bonded form a ring chosen from pyrrolidine, piperidine, N-methylpiperazine, piperazine and morpholine;

R42 is H or $C_{hh}H_{2hh+1}$;

hh is 1, 2, 3 or 4, wherein the group $C_{hh}H_{2hh+1}$ is unsubstituted or substituted where one or more H atoms are replaced by F atoms;

Y is choen from fluorine, chlorine, bromine, hydroxyl and all anionic forms of pharmacologically acceptable mono-, di- or tricarboxylic acids or sulfonic acids; and the pharmaceutically acceptable salts and trifluoroacetates thereof.

In another embodiment, compounds of the formula 1 are chosen from:

R1, R2, R3 and R4 are independently of one another H, F, Cl, Br, OH, $NH_2$, $C_aH_{2a+1}$, cycloalkyl with 3, 4, 5 or 6 C atoms, or $OC_bH_{2b+1}$;

a and b are independently of one another 1, 2, 3 or 4, wherein the groups $C_aH_{2a+1}$ and $OC_bH_{2b+1}$ independenly of one another are unsubstituted or substituted where one or more H atoms are replaced by F atoms; or R1, R2, R3 and R4 are independently of one another NR11R12;

R11 and R12 are independently of one another H, $C_eH_{2e+1}$, or $C_{rr}H_{2rr-1}$;

e is 1, 2, 3 or 4;

rr is 3, 4, 5 or 6, wherein the groups $C_eH_{2e+1}$ and $C_{rr}H_{2rr-1}$ independently of one another are unsubtituted or substituted where one or more H atoms are replaced by F atoms; or R11 and R12 together with the N atom to which they are bonded form a ring chosen from pyrrolidine, piperidine, N-methylpiperazine, piperazine and morpholine; or R11 and R12 are independently of one another COR14, CSR14, CONHR14, CSNHR14 or $SO_2R14$; wherein R14 is $C_gH_{2g+1}$;

g is 1, 2, 3 or 4, wherein the group $C_gH_{2g+1}$ is unsubstituted or substituted where one or more H atoms are replaced by F atoms; or R1, R2, R3 and R4 are independently of one another $OSO_3H$, $SO_3H$, or $SO_2R15$;

R15 is $C_kH_{2k+1}$ or NR17R18;

k is 1, 2, 3 or 4, wherein the group $C_kH_{2k+1}$ is unsubstituted or substituted where one or more H atoms are replaced by F atoms;

R17 and R18 are independently of one another H or $C_mH_{2m+1}$;

m is 1, 2, 3, 4 or 5, wherein the group $C_mH_{2m+1}$ is unsubstituted or substituted where one or more H atoms are replaced by F atoms; or R17 and R18 together with the N atom to which they are bonded form a 5- or 6-membered ring;

R5 and R6 are independently of one another methyl or trifluoromethyl;

R7 is H;

R8, R9 and R10 are independently of one another $OSO_3H$, $SO_3H$ or $SO_2R23$; wherein R23 is $C_{nn}H_{2nn+1}$ or NR25R26;

nn is 1, 2, 3, 4 or 5, wherein the group $C_{nn}H_{2nn+1}$ is unsubstituted or substituted where one or more H atoms are replaced by F atoms;

R25 and R26 are independently of one another H, CN, $C_zH_{2z+1}$, or $C_zH_{2z+1}$ in which a first $CH_2$ group bonded to the nitrogen of NR25R26 is replaced by CO or CS and a second $CH_2$ is replaced by NR27;

z is 1, 2, 3, 4, 5 or 6, wherein the group $C_zH_{2z+1}$ is unsubstituted or substituted where one ore more H atoms are replaced by F atoms;

R27 is H or $C_{aa}H_{2aa+1}$;

aa is 1, 2, 3 or 4, wherein the group $C_{aa}H_{2aa+1}$ is unsubstituted or substituted where one or more H atoms are replaced by F atoms; or R27 and a $CH_2$ group of R25 or R26 together with the N atom to which they are bonded a 5- or 6-membered ring; or R25 and R26 together with the N atom to which they are bonded form a 5- or 6-membered ring, or R8, R9 and R10 are independently of one another NR32COR30, NR32CSR30 or $NR32SO_2R30$; wherein R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;

R32 and R33 are H, methyl or $CF_3$;

cc is 1, 2, 3, 4, 5 or 6;

yy is 3, 4, 5 or 6, wherein the groups $C_{cc}H_{2cc+1}$ and $C_{yy}H_{2yy-1}$ independently of one another are unsubstituted or substituted where one ore more H atoms are replaced by F atoms and/or one or more $CH_2$ groups are replaced by O or NR31;

R31 is H, methyl, ethyl, $CF_3$, $CH_2CF_3$, acetyl or propionyl; or

R31 together with a $CH_2$ group of R30 and the N atom to which they are jointly bonded form a 5- or 6-membered ring; or R30 is pyridyl, imidazolyl, pyrazolyl, triazolyl, tetrazolyl, thiazolyl or oxazolyl, which are unsubstituted or substituted by up to 3 substituents chosen from F, Cl, methyl, ethyl, trifluoromethyl, $NH_2$, and NHacetyl; or R8, R9 and R10 are independently of one another H, F, Cl, OH, $NH_2$, $C_{ee}H_{2ee+1}$, $C_{ww}H_{2ww-1}$, $OC_{ff}H_{2ff+1}$, NR40R41, CONR40R41, COOR42 or OCOR42, ee and ff are independently of one another 1, 2, 3 or 4;

ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms; R40 and R41 are H or $C_{tt}H_{2tt+1}$;

tt is 1, 2, 3 or 4, wherein the group $C_{tt}H_{2tt+1}$ is unsubstituted or substituted where one or more H atoms are replaced by F atoms; or R40 and R41 independently of one another are hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or R40 and R41 together with the N atom to which they are bonded form a pyrrolidine, piperidine, N-methylpiperazine, piperazine or morpholine ring;
R42 is H or $C_{hh}H_{2hh+1}$;
  hh is 1, 2, 3 or 4, wherein the $C_{hh}H_{2hh+1}$ is unsubstituted or substituted where one or more H atoms are replaced by F atoms;
Y is chosen from fluorine, chlorine, bromine, hydroxyl and all anionic forms of pharmacologically acceptable mono-, di- or tricarboxylic acids and sulfonic acids;
and the pharmaceutically acceptable salts and trifluoroacetates thereof.

In another embodiment, compounds of the formula 1 are chosen from
R1 and R3 is H;
R2 and R4 are independently of one another H, F, Cl, Br, OH, $NH_2$, $C_aH_{2a+1}$, cycloalkyl with 3, 4, 5 or 6 C atoms, or $OC_bH_{2b+1}$; wherein
  a and b are independently of one another 1, 2, 3 or 4, wherein the groups $C_aH_{2a+1}$ and $OC_bH_{2b+1}$ independently of one another are unsubstituted or substituted where one or more H atoms to be replaced by F atoms;
or R2 and R4 are independently of one another NR11R12; wherein
  R11 and R12 are independently of one another H or $C_eH_{2e+1}$,
    e is 1, 2, 3 or 4, wherein the group $C_eH_{2e+1}$ is unsubstituted or substituted where one or more H atoms to be replaced by F atoms; or
  R11 and R12 together with the N atom to which they are bonded form a ring chosen from pyrrolidine, piperidine, N-methylpiperazine, piperazine and morpholine; or
  R11 and R12 are independently of one another COR14, CSR14, CONHR14, CSNHR14 or $SO_2$R14;
  R14 is $C_gH_{2g+1}$;
    g is 1, 2, 3 or 4, wherein the group $C_gH_{2g+1}$ is unsubstituted or substituted where one or more H atoms to be replaced by F atoms; or
R2 and R4 are independently of one another $OSO_3H$, $SO_3H$, or $SO_2R15$; wherein
  R15 is $C_kH_{2k+1}$ or NR17R18;
    k is 1, 2, 3 or 4, wherein the group $C_kH_{2k+1}$ is unsubstituted or substituted where one or more H atoms to be replaced by F atoms;
  R17 and R18 are independently of one another H or $C_mH_{2m+1}$;
    m is 1, 2, 3, 4 or 5, wherein the group $C_mH_{2m+1}$ is unsubstituted or substituted where one or more H atoms to be replaced by F atoms; or
  R17 and R18 together with the N atom to which they are bonded form a 5- or 6-membered ring;
R5 and R6 are independently of one another methyl or trifluoromethyl;
R7 is H;
R8, R9 and R10 are independently of one another $OSO_3H$, $SO_3H$ or $SO_2R23$; wherein
  R23 is $C_{nn}H_{2nn+1}$ or NR25R26;
    nn is 1, 2, 3, 4 or 5, wherein the group $C_{nn}H_{2nn+1}$ is unsubstituted or substituted where one or more H atoms to be replaced by F atoms;
  R25 and R26 are independently of one another H, CN, $C_zH_{2z+1}$, or $C_zH_{2z+1}$ in which a first $CH_2$ group bonded to the nitrogen of NR25R26 is replaced by CO or CS and a second $CH_2$ is replaced by NR27;
    z is 1, 2, 3, 4, 5 or 6, wherein the group $C_zH_{2z+1}$ is unsubstituted or substituted where one or more H atoms to be replaced by F atoms;
  R27 is H or $C_{aa}H_{2aa+1}$;
    aa is 1, 2, 3 or 4, wherein the group $C_{aa}H_{2aa+1}$ is unsubstituted or substituted where one or more H atoms to be replaced by F atoms or
  R27 and a $CH_2$ group of R25 or R26 together with the N atom to which they are bonded form a 5- or 6-membered ring; or
  R25 and R26 together with the N atom to which they are bonded form a 5- or 6-membered ring, or
R8, R9 and R10 are independently of one another NR32COR30, NR32CSR30 or $NR32SO_2R30$;
  R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;
  R32 and R33 are independently of one another H, methyl or $CF_3$;
    cc is 1, 2, 3, 4, 5 or 6;
    yy is 3, 4, 5 or 6, wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups are replaced by O or NR31;
  R31 is H, methyl, ethyl, $CF_3$, $CH_2CF_3$, acetyl or propionyl; or
  R31 together with a $CH_2$ group of R30 and the N atom to which they are jointly bonded form a 5- or 6-membered ring; or
  R30 is pyridyl, imidazolyl, pyrazolyl, triazolyl, tetrazolyl, thiazolyl or oxazolyl, which are unsubstituted or substituted by up to 3 substituents chosen from F, Cl, methyl, ethyl, trifluoromethyl, $NH_2$, and NHacetyl; or
R8, R9 and R10 are independently of one another H, F, Cl, OH, $NH_2$, $C_{ee}H_{2ee+1}$, $C_{ww}H_{2ww-1}$, $OC_{ff}H_{2ff+1}$, NR40R41, CONR40R41, COOR42 or OCOR42,
  ee and ff are independently of one another 1, 2, 3 or 4;
  ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms to be replaced by F atoms;
  R40 and R41 is H or $C_{tt}H_{2tt+1}$;
    tt is 1, 2, 3 or 4, wherein the group $C_{tt}H_{2tt+1}$ is unsubstituted or substituted where one or more H atoms to be replaced by F atoms; or
  R40 and R41 are independently of one another hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or
  R40 and R41 together with the N atom to which they are bonded form a pyrrolidine, piperidine, N-methylpiperazine, piperazine or morpholine ring;
  R42 is H or $C_{hh}H_{2hh+1}$;
    hh is 1, 2, 3 or 4, wherein the group $C_{hh}H_{2hh+1}$ is unsubstituted or substituted where one or more H atoms to be replaced by F atoms;
Y is chosen from fluorine, chlorine, bromine, hydroxyl and all anionic forms of pharmacologically acceptable mono-, di- or tricarboxylic acids and sulfonic acids;
and the pharmaceutically acceptable salts and trifluoroacetates thereof.

In another embodiment, compounds of the invention are chosen from the following tetrahydroisoquinolinium salts:

a. 6,8-dichloro-2,2-dimethyl-4-phenyl-1,2,3,4-tetrahydroisoquinolinium trifluoroacetate;
b. 6,8-dichloro-2,2-dimethyl-4-(4-sulfamoylphenyl)-1,2,3,4-tetrahydroisoquinolinium trifluoroacetate;
c. 4-(4-acetylaminophenyl)-6,8-dichloro-2,2-dimethyl-1,2,3,4-tetrahydroisoquinolinium iodide;
d. (+)-4-(4-acetylaminophenyl)-6,8-dichloro-2,2-dimethyl-1,2,3,4-tetrahydroisoquinolinium iodide;
e. (−)-4-(4-acetylaminophenyl)-6,8-dichloro-2,2-dimethyl-1,2,3,4-tetrahydroisoquinolinium iodide;
f. (+)-4-(4-acetylaminophenyl)-6,8-dichloro-2,2-dimethyl-1,2,3,4-tetrahydroisoquinolinium chloride;
g. 4-(4-aminophenyl)-6,8-dichloro-2,2-dimethyl-1,2,3,4-tetrahydroisoquinolinium chloride; hydrochloride;
h. 6,8-dichloro-4-[4-(3-ethylureido)phenyl]-2,2-dimethyl-1,2,3,4-tetrahydroisoquinolinium chloride;
and the pharmaceutically acceptable salts thereof.

The defined alkyl radicals and partly or completely fluorinated alkyl radicals may be both straight-chain and branched. Groups $CC_aH_{2a-1}$ and their analogs as far as $C_{yy}H_{2yy-1}$ mean either the corresponding alkenyls, cycloalkyls, cycloalkylalkyls or alkylcycloalkyl.

Heteroaryls of the invention, include, for example. 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or 5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or 5-yl, 1,2,4-oxadiazol-3-or 5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or 5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. The corresponding N-oxides of these compounds may additionally be encompassed, that is to say, for example, 1-oxy-2-, 3- or 4-pyridyl.

Of these, in one embodiment, the 5- or 6-membered heterocycles are chosen. Examples of heterocycles include imidazolyl, pyrazolyl, pyridyl, pyrrolyl, triazolyl, tetrazolyl, thiazolyl and oxazolyl.

Suitable pharmacologically acceptable anions Y are, for example, those of the following mono-, di- or tricarboxylic acids or sulfonic acids: acetic acid, adipic acid, citric acid, succinic acid, malic acid, fumaric acid, gluconic acid, glutamic acid, glycerolphosphoric acid, HCl, HBr, lactic acid, malonic acid, maleic acid, methanesulfonic acid, ethanesulfonic acid, nitric acid, di(2-hydroxy-3-carboxynaphth-1-yl)methane (pamoates), phosphoric acid, sulfuric acid, tartaric acid, toluenesulfonic acid.

In the case of multiply negatively charged acid anions, Y, it is possible for one or more cations according to the invention to be present.

If the compounds of the formula I contain one or more centers of asymmetry, these may have both the S and the R configuration. The compounds may be in the form of optical isomers, of diastereomers, of racemates or of mixtures thereof.

The terminal $CH_3$ groups in an alkyl chain are also regarded as $CH_2$ units and, in this connection, are understood as $CH_2$—H groups.

In one embodiment, suitable pharmacologically and physiologically or toxicologically acceptable salts of the compounds of the formula I are: the alkali metal salts, such as sodium or potassium salts, or the alkaline earth metal salts, e.g. calcium or magnesium salts, or the ammonium salts, e.g. salts with ammonia or organic amines or amino acids. Compounds of the formula I which have one or more basic, i.e. protonatable, groups, or contain one or more basic heterocyclic rings, may also be used in the form of their physiologically acceptable acid addition salts with inorganic or organic acids, for example as hydrochlorides, phosphates, sulfates, methanesulfonates, acetates, lactates, maleates, fumarates, malates, gluconates etc.

The salts of the following acids are, for example, also suitable in the practice of the invention: maleic acid, fumaric acid, succinic acid, malic acid, tartaric acid, methylsulfonic acid, hydrochloric acid, sulfuric acid, phosphoric acid.

The published specifications WO 01 32 624 and WO 01 32 625 describe aryl substituted tetrahydroisoquinolines, which are not quaternary compounds, as inhibitors of reuptake of norepinephrine, dopamine and serotonin. Tetrahydroisoquinolines, also not as quaternary compounds, are described in the published specification EP 11 13 007 as estrogen agonists and antagonists, while German patent application 101 59 714.2 (DEAV2001/0072) proposes the use of 4-phenyltetrahydroisoquinolines as NHE inhibitors. Methods for preparing the compounds used are also described. The synthesis of tetrahydroisoquinolines II has been described in the German patent application 101 59 714.2 (DEAV2001/0072):

Thus, in one embodiment, the compounds according to the invention can be prepared starting from the benzylamine precursors IV. These in turn may, if not obtainable commercially, be synthesized by standard processes from the corresponding benzyl chlorides or benzyl bromides III.

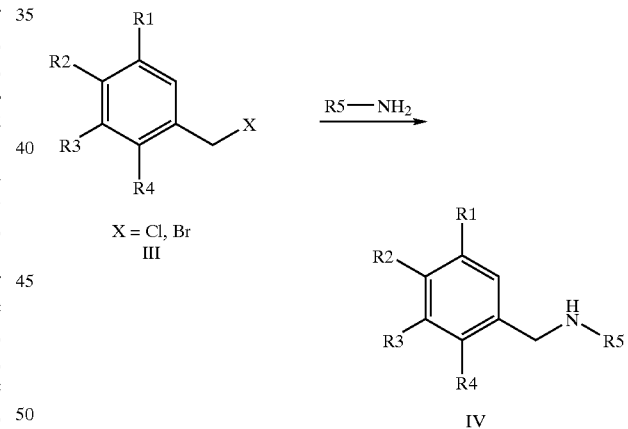

The benzylamines IV obtained in this way are alkylated in a manner known to the skilled worker with the appropriately substituted alpha-bromoacetophenone compounds V.

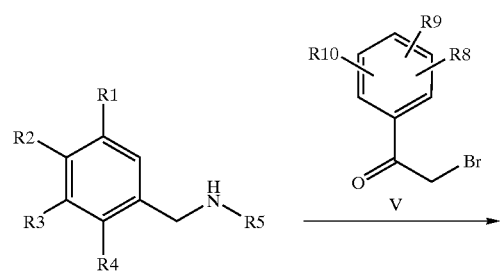

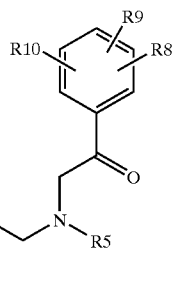

The alpha-bromacetophenone compounds V may be obtained, for example, from the corresponding acetophenone precursors by bromination in processes known from the literature. The desired tetrahydroisoquinolines II may be obtained by known processes by reduction of the carbonyl group in VI and subsequent acid-catalyzed cyclization of the corresponding alcohols VII (cf. Tetrahedron Lett.; 1989, 30, 5837; Org. Prep. Proced. Int.; 1995, 27, 513; J. Med. Chem.; 1973,16, 342).

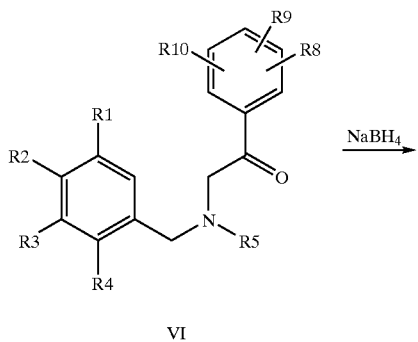

VI

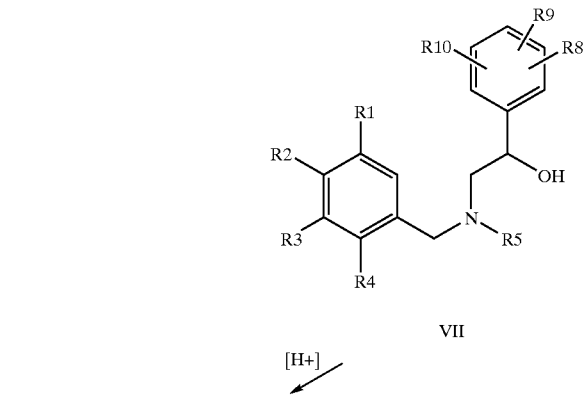

When R7 is not equal to H, the desired compounds of the formula II can be prepared for example from the iodides VIII by halogen/metal exchange and subsequent nucleophilic attack of the intermediate organolithium species on the carbonyl group (cf. Chem. Pharm. Bull.; 1995, 43, 1543).

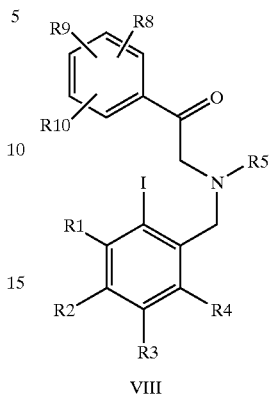

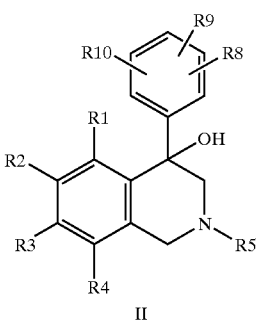

The tertiary alcohols II synthesized in this way may be converted by known methods into other derivatives.

Alkyl-branched analogs (II) may be prepared by alkylating the corresponding diphenylacetic esters X in the alpha position by known methods. The desired product XI may be converted by standard processes into the corresponding amides XII, which may be converted into the desired tetrahydroisoquinolines II in a Pictet-Spengler-analogous reaction (cf. Tetrahedron; 1987, 43, 439; Chem. Pharm. Bull.; 1985, 33, 340).

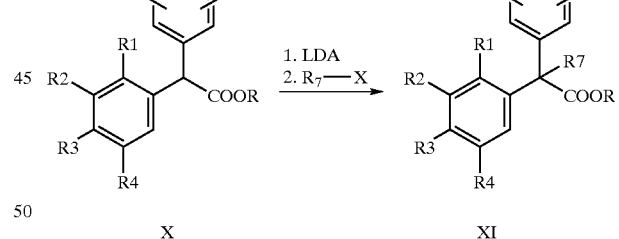

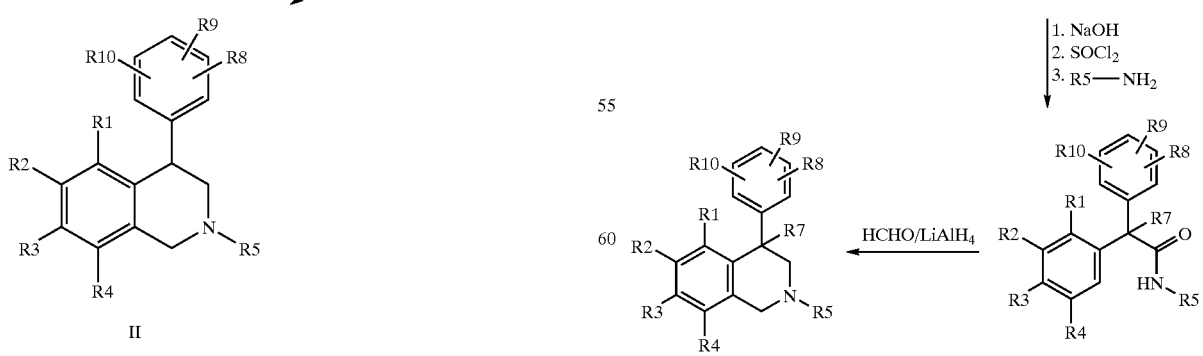

In another embodiment, the compounds of the invention can be prepared in a manner known to the skilled worker by alkylation reactions starting from II.

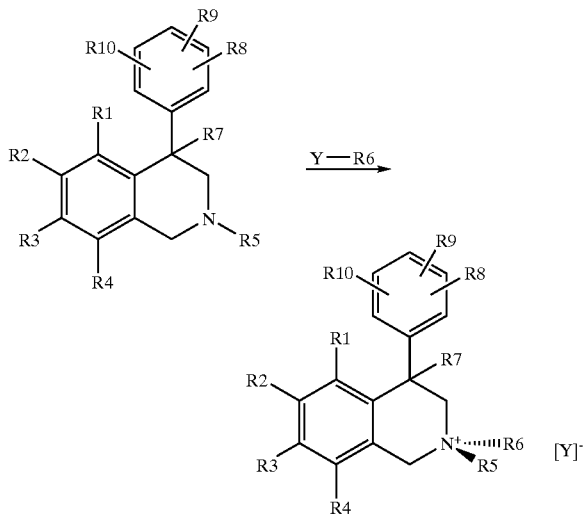

Examples of alkylating reagents which can be used are the appropriate halides, methanesulfonates, trifluoromethanesulfonates or else tosylates. The tetrahydroisoquinolinium salts produced in the reaction may easily be converted into other salts by ion exchange chromatography in a known manner.

As used herein, treating or treatment includes the treating of, for example, a patient inflicted with a disease or condition, as well as the prevention, prophylaxis, or protective treatment of a patient. Treatment also includes treating a subject susceptible to or predisposed to developing a disease or condition, which could include patients in whom a disease or condition has not yet presented as well as patients in whom the disease has been successfully treated but could redevelop or reoccur.

In one embodiment, compounds of the formula I may be excellent inhibitors of the sodium-hydrogen exchanger (NHE)—especially of the sodium-hydrogen exchanger of subtype 3 (NHE3).

On the basis of these properties, the compounds of the invention may be suitable for the treatment of disorders caused by oxygen deficiency. The compounds may be, as a result of their pharmacological properties, outstandingly suitable as antiarrhythmic medicaments with a cardioprotective component for prophylaxis of infarction and for treatment of infarction, and for the treatment of angina pectoris, in which connection they also inhibit or greatly reduce in a preventive manner the pathophysiological processes associated with the development of ischemia-induced damage, in particular in the induction of ischemia-induced cardiac arrhythmias. Because of their protective effects against pathological hypoxic and ischemic situations, the compounds of the formula I which are used according to the invention may, as a result of inhibition of the cellular $Na^+/H^+$ exchange mechanism, be used as medicaments for the treatment of all acute or chronic damage induced by ischemia or disorders induced primarily or secondarily thereby. This relates to the use thereof as medicaments for surgical interventions, e.g. in organ transplantations, in which cases the compounds can be used both to protect the organs in the donor before and during removal, to protect removed organs for example on treatment with or storage thereof in physiological bath fluids, as well as during the transfer into the recipient organism. The compounds may likewise be valuable medicaments with a protective action during the performance of angioplastic surgical interventions, for example on the heart as well as peripheral vessels. In accordance with their protective action against ischemia-induced damage, the compounds may also be suitable as medicaments for the treatment of ischemias of the nervous system, especially of the CNS, in which connection they may be suitable for example for the treatment of stroke or of cerebral edema. In addition, the compounds of the formula I which are used according to the invention may likewise be suitable for the treatment of types of shock, such as, for example, of allergic, cardiogenic, hypoglycemic and bacterial shock.

In addition, the compounds of the invention may induce an improvement in the respiratory drive and may therefore be used to treat respiratory conditions associated with the following clinical conditions and diseases: disturbance of central respiratory drive (e.g. central sleep apnea, sudden infant death, postoperative hypoxia), muscle-related breathing disorders, breathing disorders after long-term ventilation, breathing disorders associated with altitude adaptation, obstructive and mixed type of sleep apnea, acute and chronic pulmonary disorders with hypoxia and hypercapnia. The compounds additionally may increase the tone of the muscles of the upper airways, so that snoring is suppressed.

A combination of an NHE inhibitor with a carbonic anhydrase inhibitor (e.g. acetazolamide), the latter inducing metabolic acidosis and thus itself increasing respiratory activity, may provide an enhanced effect and reduced use of active ingredient.

In one embodiment, the compounds used according to the invention may have a mild laxative effect and accordingly may be used advantageously as laxatives or if there is a risk of constipation, in which case the prevention of the ischemic damage associated with constipation in the intestinal region may be provided.

In another embodiment the compounds used according to the invention may prevent the formation of gall stones.

In one embodiment, the compounds of the invention are furthermore may provide a strong inhibitory effect on the proliferation of cells, for example of fibroblast cell proliferation and the proliferation of smooth muscular muscle cells. The compounds may therefore be suitable as valuable therapeutic agents for diseases in which cell proliferation represents a primary or secondary cause, and therefore may be used as antiatherosclerotic agents, agents to prevent late complications of diabetes, cancers, fibrotic disorders such as pulmonary fibrosis, hepatic fibrosis or renal fibrosis, organ hypertrophies and hyperplasias, in particular for prostate hyperplasia or prostate hypertrophy.

The compounds used according to the invention may also be effective inhibitors of the cellular sodium-proton antiporter (Na/H exchanger) which is elevated in numerous disorders (essential hypertension, atherosclerosis, diabetes, etc.), also in those cells which are readily amenable to measurements, such as, for example, in erythrocytes, platelets or leukocytes. The compounds used according to the invention may therefore be suitable as excellent and simple scientific tools, for example in their use as diagnostic agents for determining and distinguishing different types of hypertension, but also of atherosclerosis, of diabetes, proliferative disorders etc. The compounds of the invention may moreover be suitable for preventive therapy to prevent the development of high blood pressure, for example of essential hypertension.

It has additionally been found that NHE inhibitors may show a beneficial effect on serum lipoproteins. It is generally acknowledged that blood lipid levels which are too high, so-called hyperlipoproteinemias, represent a considerable risk factor for the development of arteriosclerotic vascular lesions, especially coronary heart disease. The reduction of elevated serum lipoproteins therefore may have exceptional importance for the prophylaxis and regression of atherosclerotic lesions. The compounds used according to the invention may therefore be used for the prophylaxis and regression of atherosclerotic lesions by eliminating a causal risk factor. With this protection of the vessels against the syndrome of endothelial dysfunction, compounds of the invention may be valuable medicaments for the prevention and treatment of coronary vasospasms, of atherogenesis and of atherosclerosis, of left-ventricular hypertrophy and of dilated cardiomyopathy, and thrombotic disorders.

Compounds of the invention may also be used for: a medicament for the prevention and treatment of sleep apneas and muscle-related respiratory disorders; a medicament for the prevention and treatment of snoring; a medicament for lowering blood pressure; a medicament for the prevention and treatment of disorders induced by ischemia and reperfusion of central and peripheral organs, such as acute renal failure, stroke, endogenous states of shock, intestinal disorders etc.; a medicament for the treatment of late damage from diabetes and chronic renal disorders, in particular of all inflammations of the kidneys (nephritides) which are associated with increased protein/albumin excretion; for producing a medicament for the treatment of infection by ectoparasites in human and veterinary medicine; for producing a medicament for the treatment of said disorders in combinations with hypotensive substances, preferably with angiotensin converting enzyme (ACE) inhibitors, with diuretics and saluretics such as furosemide, hydrochlorothiazide, pseudoaldosterone antagonists and aldosterone antagonists; with adenosine receptor modulators, in particular with adenosine receptor activators (A2 agonists), and with angiotensin receptor antagonists.

In one embodiment the compounds of the invention may be sodium-proton exchange inhibitors and may be administered as novel medicaments for lowering elevated blood lipid levels, and the combination of sodium-proton exchange inhibitors with hypotensive medicaments and/or medicaments with hypolipidemic activity is envisioned.

Medicaments which comprise a compound of the invention may, for example, be administered orally, parenterally, intravenously, rectally, transdermally or by inhalation, the preferred administration being dependent on the particular characteristics of the disorder. The compounds I may moreover be used alone or together with pharmaceutical excipients, both in veterinary medicine and in human medicine.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous or intravenous administration, the active compounds used may be converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the compounds of the invention in a pharmaceutically acceptable solvent such as, in particular, ethanol or water, or a mixture of such solvents.

The formulation may, if required, also contain other pharmaceutical excipients such as surfactants, emulsifiers and stabilizers, and a propellant gas. In one embodiment, such a preparation normally contains the active ingredient in a concentration of about 0.1 to 10, in particular of about 0.3 to 3, % by weight.

The dosage of the active ingredient of the compounds of the invention to be administered, and the frequency of administration, depend on the potency and duration of action of the compounds used; additionally also on the nature and severity of the disorder to be treated and on the sex, age, weight and individual responsiveness of the mammal to be treated.

In one embodiment, on average, the daily dose of a compound of the invention for a patient weighing about 75 kg is at least 0.001 mg/kg, preferably 0.01 mg/kg, to a maximum of 10 mg/kg, preferably 1 mg/kg, of body weight. For acute episodes of the disorder, for example immediately after suffering a myocardial infarction, higher and, in particular, more frequent dosages may also be necessary, e.g. up to 4 single doses a day. Up to 200 mg a day may be necessary, in particular on i.v. administration, for example for a patient with infarction in the intensive care unit.

Descriptions of experiments and examples:
List of abbreviations used:

| | |
|---|---|
| $R_t$ | retention time |
| TFA | trifluoroacetic acid |
| HPLC | high performance liquid chromatography |
| eq | equivalent |
| LCMS | liquid chromatography mass spectroscopy |
| MS | mass spectroscopy |
| CI | chemical ionization |
| RT | room temperature |
| THF | tetrahydrofuran |
| TOTU | O-[(ethoxycarbonyl)-cyanomethyleneamino]-N,N,N',N'-tetramethyluronium tetrafluoroborate |
| DMSO | dimethyl sulfoxide |
| abs. | absolute |
| decomp. | decomposition |

General

The retention times ($R_t$) indicated below relate to LCMS measurements with the following parameters:

Method A:

| | |
|---|---|
| stationary phase: | Merck Purospher 3µ2 × 55 mm |
| mobile phase: | 95% $H_2O$ (0.05% TFA) → 95% acetonitrile; 4 min; 95% acetonitrile; 1.5 min → 5% acetonitrile; 1 min; 0.5 ml/min. |

-continued

Method A1:

| | |
|---|---|
| stationary phase: | Merck Purospher 3μ2 × 55 mm |
| mobile phase: | 95% H$_2$O (0.05% TFA) → 95% acetonitrile; 3 min; 95% acetonitrile; 1.5 min → 5% acetonitrile; 1 min; 0.5 ml/min. |

Method B:

| | |
|---|---|
| stationary phase: | Merck Purospher 3μ2 × 55 mm |
| mobile Phase: | 0 min 90% H$_2$O (0.05% TFA) 2.5 min-95% acetonitrile; 95% acetonitrile to 3.3 min; 10% acetonitrile 3.4 min; 1 ml/min. |

Method C:

| | |
|---|---|
| stationary phase: | Merck Purospher 50 × 2.5 ml |
| mobile phase: | 95% H$_2$O (0.1% HCOOH) → 95% acetonitrile; 5 min; 95% acetonitrile; 7 min; 0.45 ml/min. |

The retention times relate to the MS spectra.

The retention times relate to the MS spectra

EXAMPLE 1

6,8-Dichloro-2,2-dimethyl-4-phenyl-1,2,3,4-tetrahydroisoquinolinium, trifluoroacetate;

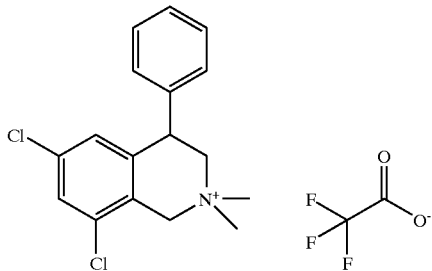

Intermediate 1

2,4-Dichlorobenzylmethylamine was prepared by methods known from the literature (J. Med. Chem.; 1984, 27, 1111).

Intermediate 2

2-[(2,4-Dichlorobenzyl)methylamino]-1-phenylethanone;

14.1 g (74.2 mmol) of intermediate 1 were dissolved in 100 ml of dioxane and, at room temperature, a solution consisting of 16.9 g (89 mmol) of 2-bromoacetophenone in 100 ml of dioxane was added dropwise. 51.2 ml (370 mmol) of triethylamine were then added, and the mixture was stirred at room temperature for four hours. After standing overnight, the resulting precipitate was filtered off with suction and the solvent was removed. The residue was dissolved in ethyl acetate and washed with 2 N HCl, H$_2$O and NaHCO$_3$. The HCl phase was adjusted to a pH of 12 with KOH and extracted twice with ethyl acetate. The combined organic phases were dried with Na$_2$SO$_4$ and concentrated. Chromatography on silica gel affords 20.6 g of the title compound as a yellow oil (R$_t$=4.188 min (method A); MS(Cl$^+$)=308.2/310.2).

Intermediate 3

2-[(2,4-Dichlorobenzyl)methylamino]-1-phenylethanol;

Intermediate 2 (20.6 g; 66.9 mol) was dissolved in 150 ml of abs. methanol and, at 0° C., 5.06 g (133.8 mmol) of sodium borohydride were added in portions. The mixture was stirred at room temperature for two hours. For workup, the solvent was removed in vacuo, and the residue was taken up in ethyl acetate and washed twice with H$_2$O. The ethyl acetate phase was dried with Na$_2$SO$_4$ and concentrated, resulting in 20 g of crude product which can be reacted further without further purification (R$_t$=4.149 min (method A); MS(Cl$^+$)=310.2/312.2).

Intermediate 4

6,8-Dichloro-2-methyl-4-phenyl-1,2,3,4-tetrahydroisoquinoline; 20 g (64.5 mmol) of intermediate 3 were dissolved in 55 ml of dichloromethane and cooled to 0° C. This solution was added dropwise to 55 ml of a precooled concentrated H$_2$SO$_4$ and subsequently stirred at room temperature for two hours. For workup, the mixture was poured onto ice and made strongly alkaline with 6 N NaOH. Three extractions with dichloromethane were carried out. The combined organic phases were dried with MgSO$_4$ and concentrated. The oily crude product was purified on silica gel, resulting in intermediate 4 in 53% yield (R$_t$=4.444 min (method A); MS(Cl$^+$)=292.2/294.2).

6,8-Dichloro-2,2-dimethyl-4-phenyl-1,2,3,4-tetrahydroisoquinolinium, trifluoroacetate; Intermediate 4 (100 mg) was dissolved in the form of its hydrochloride in acetone (1 ml) in the presence of diisopropylethylamine (58 μl). Methyl iodide (38 μl) was then added dropwise with stirring. The mixture was then stirred at room temperature for two hours and subsequently left to stand for 62 h. Since the reaction was still not complete, further methyl iodide (38 μl) was added and the mixture was heated to reflux. After two hours, the reaction mixture was cooled and then concentrated to dryness in a rotary evaporator. The residue was purified by preparative HPLC on RP-18 with acetonitrile/water (0.05% TFA), and the pure fractions were combined. The acetonitrile was stripped off and then the aqueous residue was freeze dried. 132 mg of the desired product were obtained as a solid. (R$_t$=4.22 min (method A); MS (Cl$^+$): 306.0).

EXAMPLE 2

6,8-Dichloro-2,2-dimethyl-4-(4-sulfamoylphenyl)-1,2,3,4-tetrahydroisoquinolinium, Trifluoroacetate;

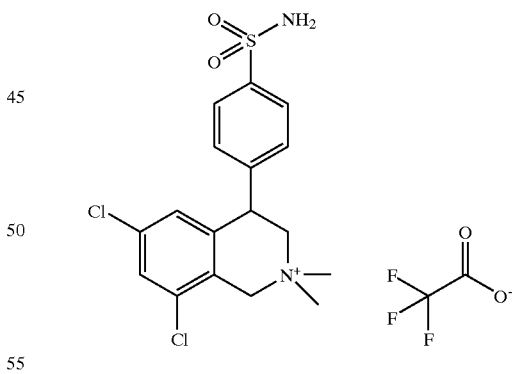

Intermediate 1

4-(6,8-Dichloro-2-methyl-1,2,3,4-tetrahydroisoquinolin-4-yl)benzenesulfonamide;

A solution of 3.0 g (10 mmol) of 6,8-dichloro-2-methyl-4-phenyl-1,2,3,4-tetrahydroisoquinoline (intermediate 4, example 1) in 30 ml of dichloromethane was slowly added dropwise at 0° C. to 10 ml (150 mmol) of chlorosulfonic acid. The mixture was stirred at 0° C. for one hour and at room temperature for one hour. For workup, the reaction mixture was poured onto ice and a pH of 8 was set with saturated NaHCO$_3$ solution. After three extractions with ethyl acetate, the organic phases were dried with Na$_2$SO$_4$ and concentrated. The crude product (3.34 g) obtained in this way was suspended in 200 ml of concentrated ammonia and heated to 90° C. After three hours, the solvent was distilled off and the residue was taken up in a little H$_2$O and extracted three times with ethyl acetate. The combined ethyl acetate phases were dried with Na$_2$SO$_4$ and concentrated, resulting in 2.76 g of an amorphous crude product. Further purification by separation on a silica gel column (dichloromethane/methanol 95:5) results in 830 mg of the desired sulfonamide.

6,8-Dichloro-2,2-dimethyl-4-(4-sulfamoylphenyl)-1,2,3,4-tetrahydroisoquinolinium, Trifluoracetate;

371 mg (1.0 mmol) of intermediate 1 were dissolved in 10 ml of DMF and, at room temperature, 11 eq. of methyl iodide are added. After three hours, the solvent was removed and the residue was digested in H$_2$O. Drying over P$_2$O$_5$ results in 380 mg of crude product which is purified on a preparative HPLC. (R$_t$=3.583 min (method A); MS(ES$^+$)=385.0/387.0).

EXAMPLE 3

3a: 4-(4-Acetylaminophenyl)-6,8-dichloro-2,2-dimethyl-1,2,3,4-tetrahydroisoquinolinium iodide;

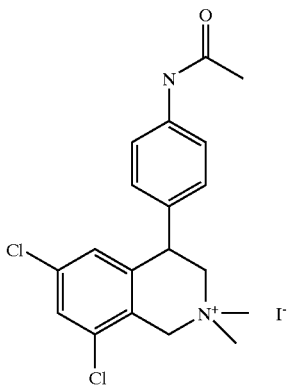

3b: (+)-4-(4-Acetylaminophenyl)-6,8-dichloro-2,2-dimethyl-1,2,3,4-tetrahydroisoquinolinium iodide;

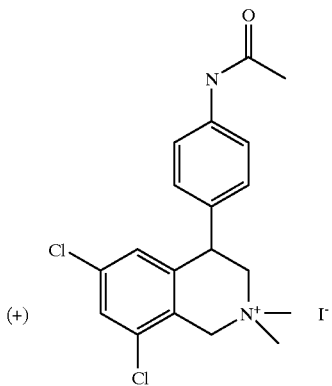

3c: (+)-4-(4-Acetylaminophenyl)-6,8-dichloro-2,2-dimethyl-1,2,3,4-tetrahydroisoquinolinium chloride;

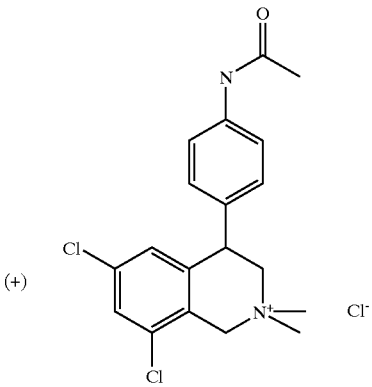

3d: (−)-4-(4-Acetylaminophenyl)-6,8-dichloro-2,2-dimethyl-1,2,3,4-tetrahydroisoquinolinium iodide;

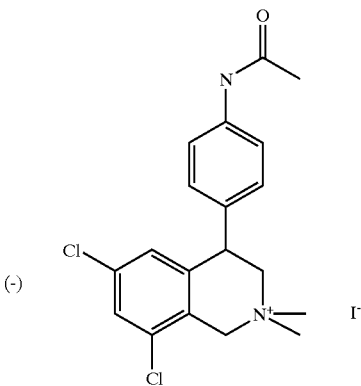

Intermediate 1

2,4-Dichlorobenzylmethylamine was prepared by methods known from the literature (J. Med. Chem.; 1984, 27, 1111).

Intermediate 2

N-[4-(2-Bromoacetyl)phenyl]acetamide was synthesized in a manner known to the skilled worker by bromination of N-(4-acetylphenyl)acetamide.

The starting compound (0.256 mol) was introduced into 300 ml of acetic acid and, at 60° C., a solution of 39.9 g of bromine (1.0 eq) in 60 ml of acetic acid was added dropwise. After 1.5 h, the reaction mixture was allowed to cool to room temperature and was added to 1 l of ice water. The precipitate was filtered off with suction, washed with water and dried, with 60 g of the title compound being isolated (m.p.: 192° C.).

Intermediate 3

N-(4-{2-[(2,4-Dichlorobenzyl)methylamino]acetyl}phenyl)acetamide;

37.1 g (0.195 mol) of intermediate 1 were introduced into 400 ml of dioxane, and a solution of 60 g (0.234 mol) of intermediate 2 in 600 ml of dioxane was added. 134 ml of triethylamine were added, and the mixture was stirred at room temperature for 4 h. After standing overnight, the precipitate was filtered off and the filtrate is concentrated in vacuo. The residue was taken up in ethyl acetate, washed with NaHCO$_3$ and H$_2$O, dried with MgSO$_4$ and concentrated. The oily residue resulting from this was triturated with an ethyl acetate/ether mixture, resulting in 36 g of intermediate 3 in the form of a crystalline solid (m.p.: 115–117° C.).

Intermediate 4

N-(4-{2-[(2,4-Dichlorobenzyl)methylamino]-1-hydroxyethyl}phenyl)acetamide;

36 g (0.099 mol) of intermediate 3 were dissolved in 500 ml of methanol and, at 0° C., 7.8 g (2 eq) of sodium borohydride were added. The mixture was stirred at 0° C. for 30 min and at room temperature for a further hour. For workup, the reaction mixture was concentrated and the residue was partitioned between 1 N HCl and ethyl acetate. The aqueous phase was separated off, adjusted to pH 9 and extracted twice with ethyl acetate. The combined organic phases were dried with $MgSO_4$ and concentrated. The crude product obtained in this way can be reacted further without further purification.

Intermediate 5

N-[4-(6,8-Dichloro-2-methyl-1,2,3,4-tetrahydroisoquinolin-4-yl)phenyl]acetamide;

20 g (0.054 mol) of intermediate 4 were dissolved in 250 ml of dichloromethane and, at 0° C., 250 ml of concentrated $H_2SO_4$ were added dropwise. The mixture was stirred at 0° C. for two hours and at room temperature for a further hour. For workup, the reaction mixture was added to ice water, and the precipitate was filtered off with suction. The precipitate was taken up in 300 ml of 1 N NaOH and extracted three times with ethyl acetate. Drying of the organic phase and concentration afford a crude product which was triturated with diisopropyl ether, with 11.7 g of the compound of the example being isolated as crystalline solid (m.p.: 205–206° C.).

4-(4-Acetylaminophenyl)-6,8-dichloro-2,2-dimethyl-1,2,3,4-tetrahydroisoquinolinium iodide (example 3a);

2.0 g (5.7 mmol) of intermediate 5 were introduced into 60 ml of abs. DMF and, at room temperature, 3.6 ml (60.0 mmol) of methyl iodide were added. The mixture was stirred at room temperature for three hours and then concentrated in vacuo. The residue was stirred once with a little $H_2O$, filtered off with suction and extracted once again with boiling ethyl acetate. Filtration with suction affords 2.65 g of a pale yellow solid as crude product. 1.0 g of this was dissolved in 250 ml of $H_2O$ and extracted with 100 ml of ethyl acetate. The aqueous phase was filtered and concentrated, resulting in 837 mg of the desired ammonium iodide in the form of a colorless solid. ($R_t$=3.804 min (method A); MS(ES$^+$)=363.1/365.1).

2.0 g of intermediate 5 were separated into the enantiomers on a chiral phase.

Conditions:

stationary phase: Chiralpak AD 250×4.6; 20 μm;
mobile phase: acetonitrile
flow rate: 1 ml/min
$R_t$(enantiomer 1)=5.856 min, (−) enantiomer, about 850 mg;
$R_t$(enantiomer 2)=8.613 min; (+) enantiomer, about 850 mg.

(+)-4-(4-Acetylaminophenyl)-6,8-dichloro-2,2-dimethyl-1,2,3,4-tetrahydroisoquinolinium iodide (Example 3b);

500 mg (1.43 mmol) of the (+) enantiomer of intermediate 5 (enantiomer 2) were reacted with methyl iodide in analogy to the synthesis method indicated in example 3a, resulting in 500 mg of the desired enantiopure ammonium iodide in the form of a colorless solid. ($R_t$=1.630 min (method B); MS(ES$^+$)=363.2/365.2).

(+)-4-(4-Acetylaminophenyl)-6,8-dichloro-2,2-dimethyl-1,2,3,4-tetrahydroisoquinolinium Chloride (Example 3c);

15 g of ion exchange resin (Amberlite IRA-93) were stirred in 2 N NaOH for 30 min and then packed into a column. It was washed with $H_2O$ until a pH check indicates a neutral reaction. The exchange resin was stirred twice in 2 N HCl for 15 min, packed into a column and again washed with $H_2O$ until a pH check again indicates a neutral reaction. A solution of 400 mg of the compound of example 3b in 60 ml of $H_2O$ was passed over the resin (HCl form) prepared in this way and eluted with $H_2O$. Concentration of the product fractions affords 303 mg of the desired chloride salt as colorless solid. ($R_t$=1.990 min (method C); MS(ES$^+$)=363.2/365.2).

(−)-4-(4-Acetylaminophenyl)-6,8-dichloro-2,2-dimethyl-1,2,3,4-tetrahydroisoquinolinium, iodide (Example 3d);

A procedure analogous to the method described for the compound of example 3b, starting from the (−) enantiomer of intermediate 5 (enantiomer 1), affords the corresponding enantiopure product 3d with the opposite configuration to 3b. ($R_t$=1.952 min (method A1); MS(ES$^+$)=363.2/365.2).

EXAMPLE 4

4-(4-Aminophenyl)-6,8-dichloro-2,2-dimethyl-1,2,3,4-tetrahydroisoquinolinium chloride, hydrochloride;

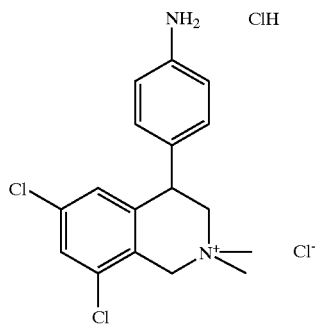

3.5 g (7.13 mmol) of 4-(4-acetylaminophenyl)-6,8-dichloro-2,2-dimethyl-1,2,3,4-tetrahydroisoquinolinium iodide (example 3a) were heated to reflux in 490 ml of 10% strength HCl and 112 ml of ethanol for two hours. After cooling to room temperature, the mixture was concentrated in vacuo, and the residue was partitioned between $H_2O$ and ethyl acetate. The aqueous phase was concentrated to a volume of about 200 ml and subjected to an ion exchange chromatography by the method described in example 3c. Concentration of the eluate affords 2.1 g of the desired hydrochloride. ($R_t$=1.634 min (method A1); MS(ES$^+$)=321.0/323.1).

EXAMPLE 5

6,8-Dichloro-4-[4-(3-ethylureido)phenyl]-2,2-dimethyl-1,2,3,4-tetrahydroisoquinolinium chloride;

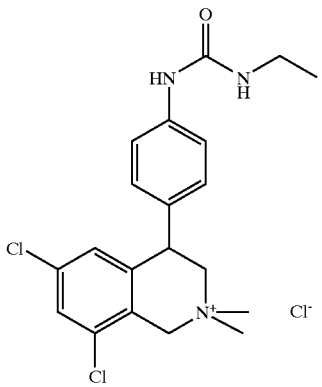

Intermediate 1

4-(6,8-Dichloro-2-methyl-1,2,3,4-tetrahydroisoquinolin-4-yl)phenylamine;

3.0 g (8.59 mmol) of N-[4-(6,8-dichloro-2-methyl-1,2,3,4-tetrahydroisoquinolin-4-yl)-phenyl]acetamide (example 3, intermediate 5) were heated to reflux in 100 ml of 21% strength sodium ethanolate solution. Solid sodium ethanolate was added depending on the progress of the reaction, until complete conversion was achieved. For workup, the solvent was removed and the residue was taken up in $H_2O$. It was extracted twice with dichloromethane. The combined organic phases were dried with $MgSO_4$ and concentrated. Further purification takes place by chromatography on silica gel with an ethyl acetate/heptane mixture, resulting in the aniline compound as a yellow oil.

Intermediate 2

1-[4-(6,8-Dichloro-2-methyl-1,2,3,4-tetrahydroisoquinolin-4-yl)phenyl]-3-ethylurea, Hydrochloride;

500 mg (1.63 mmol) of 4-(6,8-dichloro-2-methyl-1,2,3,4-tetrahydroisoquinolin-4-yl)phenylamine were introduced into 20 ml of toluene, and a solution of 284 mg (4.0 mmol) of ethyl isocyanate in a little toluene is added dropwise. After one hour at 80° C., a further 180 mg of ethyl isocyanate are added, and the mixture was stirred at 80° C. for one hour. For workup, the solvent was removed and the residue was triturated with $H_2O$ and ethyl acetate, filtered off with suction and dried, resulting in the title compound as a pale yellowish solid (m.p.: 218–220° C.). The ethylurea obtained in this way was converted into the corresponding hydrochloride in a manner known to the skilled worker.

6,8-Dichloro-4-[4-(3-ethylureido)phenyl]-2,2-dimethyl-1,2,3,4-tetrahydroisoquinolinium chloride;

1-[4-(6,8-Dichloro-2-methyl-1,2,3,4-tetrahydroisoquinolin-4-yl)phenyl]-3-ethylurea hydrochloride (300 mg, 0.72 mmol) was partitioned between $NaHCO_3$ and ethyl acetate. The resulting precipitate was filtered off with suction, dried and dissolved in 20 ml of DMF. Addition of 1.14 g (8.03 mmol) of methyl iodide was followed by stirring at room temperature for three hours. For workup, the solvent was removed, and the residue was taken up in $H_2O$ and extracted with ethyl acetate. The aqueous phase was concentrated in vacuo, and the residue was triturated once again with ethyl acetate and filtered off with suction. The quaternary ammonium salt obtained in this way was subjected to an ion exchange chromatography by the method described in example 3c. Concentration of the eluate affords 90 mg of the desired chloride. ($R_t$=2.028 min (method A1); $MS(ES^+)$=392.3,0/394.2).

Pharmacological Data

Description of Test

In this test, the recovery in the intracellular pH ($pH_i$) after an acidification is ascertained, which is initiated if the NHE is capable of functioning, even under bicarbonate-free conditions. For this purpose, the $pH_i$ was determined using the pH-sensitive fluorescent dye BCECF (Calbiochem, the precursor BCECF-AM is employed). The cells were initially loaded with BCECF. The BCECF fluorescence was determined in a "Ratio Fluorescence Spectrometer" (Photon Technology International, South Brunswick, N.J., USA) at excitation wavelengths of 505 and 440 nm and an emission wavelength of 535 nm and converted into the $pH_i$ using calibration curves. The cells were incubated in $NH_4Cl$ buffer (pH 7.4) ($NH_4Cl$ buffer: 115 mM NaCl, 20 mM $NH_4Cl$, 5 mM KCl, 1 mM $CaCl_2$, 1 mM $MgSO_4$, 20 mM Hepes, 5 mM glucose, 1 mg/ml BSA; a pH of 7.4 was adjusted with 1 M NaOH) even during the BCECF loading. The intracellular acidification was induced by adding 975 µl of an $NH_4Cl$-free buffer (see below) to 25 µl aliquots of the cells incubated in $NH_4Cl$ buffer. The subsequent rate of pH recovery was recorded for two minutes with NHE1, five minutes with NHE2 and three minutes with NHE3. To calculate the inhibitory potency of the tested substances, the cells were initially investigated in buffers with which a complete or absolutely no pH recovery took place. For complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM Hepes, 5 mM glucose, a pH of 7.0 is adjusted with 1 M NaOH). To determine the 0% value, the cells were incubated in an $Na^+$-free buffer (133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM Hepes, 5 mM glucose, a pH of 7.0 is adjusted with 1 M NaOH). The substances to be tested were made up in the $Na^+$-containing buffer. The recovery of the intracellular pH at each test concentration of a substance was expressed as a percentage of the maximum recovery. The $IC_{50}$ value for the particular substance for the individual NHE subtypes was calculated from the pH recovery percentages using the Sigma-Plot program.

Results

| Example | $IC_{50}$ [µM], (rNHE3) |
|---|---|
| 1 | 0.23 |
| 2 | 0.90 |
| 3a | 0.67 |
| 3c | 0.43 |
| 4 | 0.03 |

What is claimed is:
1. A compound of the formula I

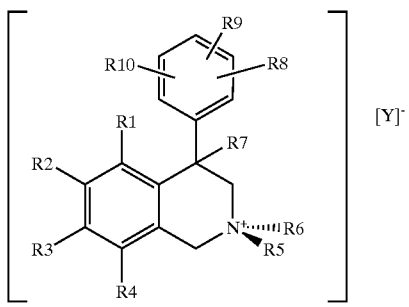

wherein:
R1, R2, R3 and R4 are independently of one another H, F, Cl, Br, I, CN, NO$_2$, OH, NH$_2$, C$_a$H$_{2a+1}$, C$_{qq}$H$_{2qq-1}$, OC$_b$H$_{2b+1}$, COOR50, OCOR50, COR50 or O$_x$—(CH$_2$)$_y$-phenyl; wherein
  a and b are independently of one another 1, 2, 3, 4, 5, 6, 7 or 8, wherein the groups C$_a$H$_{2a+1}$ and OC$_b$H$_{2b+1}$ independently of one another are unsubstituted or substituted where one or more H atoms are replaced by F atoms;
  qq is 3, 4, 5, 6, 7 or 8, wherein the group C$_{qq}$H$_{2qq-1}$ is unsubstituted or substituted where one or more H atoms are replaced by F atoms;
  R50 is H or C$_c$H$_{2c+1}$,
    c is 1, 2, 3, 4, 5, 6, 7 or 8, wherein the group C$_c$H$_{2c+1}$ is unsubstituted or substituted where one or more H atoms are replaced by F atoms;
  x is zero or 1;
  y is zero, 1, 2, 3 or 4, where the phenyl ring in the group O$_x$—(CH$_2$)$_y$-phenyl is unsubstituted or substituted by 1–3 independently chosen from F, Cl, Br, CN, NO$_2$, OH, NH$_2$ and C$_d$H$_{2d+1}$,
    d is 1, 2, 3 or 4, wherein the group C$_d$H$_{2d+1}$ is unsubstituted or substituted where one or more H atoms are replaced by F atoms; or
R1, R2, R3 and R4 are independently of one another chosen from a heteroaryl with at least one heteroatom chosen from 1, 2, 3 or 4 N atoms, 1 oxygen atom and 1 S atom, present as a ring atom; or
R1, R2, R3 and R4 are independently of one another CONR11R12 or NR11R12; wherein
  R11 and R12 are independently of one another H, C$_e$H$_{2e+1}$ or C$_{rr}$H$_{2rr-1}$,
    e is 1, 2, 3, 4, 5, 6, 7 or 8;
    rr is 3, 4, 5, 6, 7, or 8, wherein the groups C$_e$H$_{2e+1}$ and C$_{rr}$H$_{2rr-1}$ independently of one another are unsubstituted or substituted where one or more H atoms are replaced by F atoms and/or one or more CH$_2$ groups are replaced by O or NR13;
  R13 is H or C$_f$H$_{2f+1}$;
    f is 1, 2, 3 or 4, wherein the group C$_f$H$_{2f+1}$ is unsubstituted or substituted where one or more H atoms are replaced by F atoms; or
  R13 and a CH$_2$ group of R11 or R12 together with the N atom to which they are bonded form a 5- or 6-membered ring; or
  R11 and R12 together with the N atom to which they are bonded form a 5-, 6- or 7-membered ring; or
  R11 and R12 are independently of one another COR14, CSR14 or SO$_2$R14; wherein
    R14 is C$_g$H$_{2g+1}$;
      g is 1, 2, 3, 4, 5, 6, 7 or 8, wherein the group C$_g$H$_{2g+1}$ is unsubstituted or substituted where one or more H atoms are replaced by F atoms, and/or one or more CH$_2$ groups are replaced by O or NR13; or
R1, R2, R3 and R4 are independently of one another —O$_h$—SO$_j$—R15; wherein
  h is zero or 1;
  j is zero, 1 or 2;
  R15 is C$_k$H$_{2k+1}$, OH, OC$_l$H$_{2l+1}$ or NR17R18;
    k is 1, 2, 3, 4, 5, 6, 7 or 8, wherein the group C$_k$H$_{2k+1}$ is unsubsitituted or substituted where one or more H atoms are replaced by F atoms;
    l is 1, 2, 3, 4, 5, 6, 7 or 8, wherein the group OC$_l$H$_{2l+1}$ is unsubsitituted or substituted where one or more H atoms are replaced by F atoms;
  R17 and R18 are independently of one another H or C$_m$H$_{2m+1}$;
    m is 1, 2, 3, 4, 5, 6, 7 or 8, wherein the group C$_m$H$_{2m+1}$ is unsubstituted or substituted where one or more H atoms is replaced by F atoms and/or one or more CH$_2$ groups are replaced by O, CO, CS or NR19;
    R19 is H or C$_n$H$_{2n+1}$;
      n is 1, 2, 3 or 4, wherein the group C$_n$H$_{2n+1}$ is unsubstituted or substituted where one or more H atoms are replaced by F atoms; or
  R17 and R18 together with the N atom to which they are bonded form a 5-, 6- or 7-membered ring; or
  R19 and a CH$_2$ group of R17 or R18 together with the N atom
    to which they are bonded form a 5- or 6-membered ring; with the proviso that R2 is not H;
R5 and R6 are independently of one another C$_p$H$_{2p+1}$, C$_{ss}$H$_{2ss-1}$, COR20 or SO$_2$R20; wherein
  p is 1, 2, 3, 4, 5, 6, 7 or 8;
  ss is 3, 4, 5, 6, 7 or 8;
R20 is C$_q$H$_{2q+1}$;
  q is 1, 2, 3, 4, 5, 6, 7 or 8, wherein the groups C$_p$H$_{2p+1}$, C$_{ss}$H$_{2ss-1}$ and C$_q$H$_{2q+1}$ independently of one another are unsubstituted or substituted where one or more H atoms are replaced by F atoms and/or one or more CH$_2$ groups are replaced by O or NR21;
R21 is H or C$_r$H$_{2r+1}$;
  r is 1, 2, 3 or 4; wherein the group C$_r$H$_{2r+1}$ is unsubstituted or substituted where one or more H atoms are replaced by F atoms;
R7 is H, F, Cl, Br, I, C$_s$H$_{2s+1}$, C$_{dd}$H$_{2dd-1}$, OH, OC$_t$H$_{2t+1}$ or OCOR22; wherein s and t are independently of one another 1, 2, 3, 4, 5, 6, 7 or 8;
  dd is 3, 4, 5, 6, 7 or 8, wherein the groups C$_s$H$_{2s+1}$, C$_{dd}$H$_{2dd-1}$ and OC$_t$H$_{2t+1}$ independently of one another are unsubstituted or substituted where one or more H atoms are replaced by F atoms;
R22 is C$_u$H$_{2u+1}$;
  u is 1, 2, 3 or 4, wherein the group C$_u$H$_{2u+1}$ is unsubstituted or substituted where one or more H atoms are replaced by F atoms;
R8, R9 and R10 are independently of one another —O$_v$—SO$_w$—R23; wherein
  v is zero or 1;
  w is zero, 1 or 2;
R23 is C$_{nn}$H$_{2nn+1}$, C$_{mm}$H$_{2mm-1}$, OH, OC$_{pp}$H$_{2pp+1}$ or NR25R26;
  nn and pp are independently of one another 1, 2, 3, 4, 5, 6, 7 or 8, mm is 3, 4, 5, 6, 7 or 8, wherein the groups $C_{nn}H_{2nn+1}$, $C_{mm}H_{2mm-1}$ and $OC_{pp}H_{2pp+1}$ independently of one another are unsubstituted or substituted where one or more H atoms are replaced by F atoms;

R25 and R26 are independently of one another H, CN, $C_zH_{2z+1}$, or $C_{zz}H_{2zz-1}$;

z is 1, 2, 3, 4, 5, 6, 7 or 8;

zz is 3, 4, 5, 6, 7 or 8, wherein the group $C_zH_{2z+1}$ is unsubstituted or substituted where one or more H atoms are replaced by F atoms and, wherein the group $C_zH_{2z+1}$, is unsubstituted or substituted where one or more H atoms are replaced by F atoms and/or one or more $CH_2$ groups are replaced by O, CO, CS or NR27;

R27 is H or $C_{aa}H_{2aa+1}$;

aa is 1, 2, 3 or 4, wherein the group $C_{aa}H_{2aa+1}$ is unsubstituted or substituted where one or more H atoms are replaced by F atoms; or R27 and a $CH_2$ group of R25 or R26 together with the N atom to which they are bonded form a 5- or 6-membered ring; or R25 and R26 together with the N atom to which they are bonded form a 5-, 6- or 7-membered ring, or R8, R9 and R10 are independently of one another $NR32COR30$, $NR32CSR30$ or $NR32SO_{bb}R30$; wherein R30 is H, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;

R32 and R33 are independently of one another H or $C_hH_{2h+1}$;

bb is 2 or 3;

cc is 1, 2, 3, 4, 5, 6, 7 or 8;

yy is 3, 4, 5, 6, 7 or 8;

h is 1, 2, 3, 4, 5, 6, 7 or 8, wherein the group $C_hH_{2h+1}$ is unsubstituted or substituted where one or more H atoms are replaced by F atoms, and wherein the groups $C_{cc}H_{2cc+1}$ and $C_{yy}H_{2yy-1}$ independently of one another are unsubstituted or substituted where one or more H atoms are replaced by F atoms and/or one or more $CH_2$ groups are replaced by O or NR31;

R31 is H, $C_{kk}H_{2kk+1}$, or COR65;

kk is 1, 2, 3, or 4; wherein the group $C_{kk}H_{2kk+1}$ is unsubstituted or substituted where one or more H atoms are replaced by F atoms, R65 is H, or $C_{xx}H_{2xx+1}$;

xx is 1, 2, 3 or 4, wherein the group $C_{xx}H_{2xx+1}$ is unsubstituted or substituted where one or more H atoms are replaced by F atoms; or R31 together with a $CH_2$ group of R30 and the N atom to which they are jointly bonded forms a 5-, 6- or 7-membered ring; or R30 is a 5- or 6-membered heteroaryl with at least one hetero atom chosen from 1, 2, 3 or 4 N atoms, 1 S atoms and 1 O atoms which is unsubstituted or substituted by up to three substituents chosen from F, Cl, Br, I, $C_{oo}H_{2oo+1}$, and NR70R71;

R70 and R71 are independently of one another H, $C_{uu}H_{2uu+1}$ or COR72

R72 is H, or $C_{vv}H_{2vv+1}$; oo, uu and vv are independently of one another 1, 2, 3, 4, 5, 6, 7 or 8, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms; or R8, R9 and R10 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 or OCOR42;

ee and ff are independently of one another 1, 2, 3, 4, 5, 6, 7 or 8;

ww is 3, 4, 5, 6, 7 or 8, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms;

R40 and R41 are independently of one another H or $C_{tt}H_{2tt+1}$;

tt is 1, 2, 3, 4, 5, 6, 7 or 8, wherein the group $C_{tt}H_{2tt+1}$ is unsubstituted or substituted where one or more H atoms are replaced by F atoms and/or where one or more $CH_2$ groups are replaced by O or NR44;

R44 is H or $C_{gg}H_{2gg+1}$;

gg is 1, 2, 3, 4, 5, 6, 7 or 8, wherein the group $C_{gg}H_{2gg+1}$ is unsubstituted or substituted where one or more H atoms are replaced by F atoms; or R40 and R41 with the N atom to which they are bonded for a 5- or 6-membered ring;

R42 is H or $C_{hh}H_{2hh+1}$;

hh is 1, 2, 3, 4, 5, 6, 7 or 8, wherein the group $C_{hh}H_{2hh+1}$ is unsubstituted or substituted where one or more H atoms are replaced by F atoms;

Y is chosen from fluorine, chlorine, bromine, iodine, hydroxyl and all anionic forms of pharmacologically acceptable mono-, di- or tricarboxylic acids and sulfonic acids;

or a pharmaceutically acceptable salt thereof, or a trifluoroacetic acid salt thereof, in any stereoisomeric form, or a mixture of any such compounds in any ratio.

2. A compound as claimed in claim 1, in which

R1, R2, R3 and R4 are independently of one another, H, F, Cl, Br, I, CN, $NO_2$, OH, $NH_2$, $C_aH_{2a+1}$, cycloalkyl with 3, 4, 5 or 6 C atoms, $OC_bH_{2b+1}$, or COOR50; wherein a and b are independently of one another 1, 2, 3 or 4, wherein the group $C_aH_{2a+1}$ is unsubstituted or substituted where one or more H atoms are replaced by F atoms;

R50 is H or $C_cH_{2c+1}$;

c is 1, 2, 3 or 4, wherein the group $C_cH_{2c+1}$ is unsubstituted or substituted where one or more H atoms are replaced by F atoms;

or R1, R2, R3 and R4 are independently of one another a 5- or 6-membered heteroaryl chosen from imidazolyl, pyrazolyl, pyrrolyl, triazolyl, tetrazolyl, thiazolyl and oxazolyl; or R1, R2, R3 and R4 are independently of one another CONR11 R12 or NR11R12; wherein R11 and R12 are independently of one another H, $C_eH_{2e+1}$, or $C_{rr}H_{2rr-1}$;

e is 1, 2, 3 or 4;

rr is 3, 4, 5 or 6, wherein the groups $C_eH_{2e+1}$ and $C_{rr}H_{2rr-1}$ independently of one another are unsubstituted or substituted where one or more H atoms are replaced by F atoms; or R11 and R12 independently of one another are hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or R11 and R12 together with the N atom to which they are bonded form a pyrrolidine, piperidine, N-methylpiperazine, piperazine or morpholine ring; or R11 and R12 are independently of one another COR14, CSR14, CCNHR14, CSNHR14 or $SO_2R14$; wherein R14 is $C_gH_{2g+1}$;
  g is 1, 2, 3 or 4, wherein the group $C_gH_{2g+1}$ is unsubstituted or substituted where one or more H atoms are replaced by F atoms; or R1, R2, R3 and R4 are independently of one another $OSO_3H$, $SO_3H$, $SO_2R_{15}$; wherein R15 is $C_kH_{2k+1}$, $OC_lH_{2l+1}$ or NR17R18;
  k 1, 2, 3 or 4, wherein the group $C_kH_{2k+1}$ is unsubstituted or substituted where one or more H atoms are replaced by F atoms;
  l 1, 2, 3 or 4, wherein the group $OC_lH_{2l+1}$ is unsubstituted or substituted where one or more H atoms are replaced by F atoms;

R17 and R18 are independently of one another H, $C_mH_{2m+1}$ or $C_mH_{2m+1}$, in which a first $CH_2$ group bonded to the nitrogen of NR17R18 is replaced by CO and a second $CH_2$ group is replaced by NR19;
  m 1, 2, 3, 4 or 5, wherein the group $C_mH_{2m+1}$ is unsubstituted or substituted where one or more H atoms is replaced by F atoms;

R19 is H or $C_nH_{2n+1}$;
  n is 1, 2, 3 or 4, wherein the group $C_nH_{2n+1}$ is unsubstituted or substituted where one or more H atoms is replaced by F atoms; or R17 and R18 together with the N atom to which they are bonded a 5- or 6-membered ring;

with the proviso that R2 is not H;

R5 and R6 are independently of one another $C_pH_{2p+1}$;
  p is 1, 2, 3 or 4, wherein the group $C_pH_{2p+1}$ is unsubstituted or substituted where one or more H atoms is replaced by F atoms;

R7 is H, $C_sH_{2s+1}$, $OC_tH_{2t+1}$ or OCOR22; wherein
  s and t are independently of one another 1, 2, 3 or 4, wherein the groups $C_sH_{2s+1}$ and $OC_tH_{2t+1}$ independently of another are unsubstituted or substituted where one or more H atoms is replaced by F atoms;

R22 is $C_uH_{2u+1}$;
  u is 1, 2, 3 or 4; wherein the group $C_uH_{2u+1}$ is unsubstituted or substituted where one or more H atoms is replaced by F atoms;

R8, R9 and R10 are independently of one another $OSO_3H$, $SO_3H$ or $SO_2R23$; wherein R23 is $C_{nn}H_{2nn-1}$, $C_{mm}H_{2mm-1}$, $OC_{pp}H_{2pp+1}$ or NR25R26; nn and pp are independently of one another 1, 2, 3, 4 or 5, mm is 3, 4, 5 or 6, wherein the groups $C_{nn}H_{2nn+1}$, $C_{mm}H_{2mm-1}$ and $OC_{pp}H_{2pp+1}$ independently of another are unsubstituted or substituted where one or more H atoms is replaced by F atoms;

R25 and R26 are independently of one another H, CN, $C_zH_{2z+1}$ or $C_zH_{2z+1}$, in which a first $CH_2$ group bonded to the nitrogen of NR25R26 is replaced by CO or OS and a second $CH_2$ is replaced by NR27;
  z is 1, 2, 3, 4, 5 or 6; wherein the group $O_zH_{2z+1}$ is unsubstituted or substituted where one or more H atoms are replaced by F atoms;

R27 is H or $C_{aa}H_{2aa+1}$;
  aa is 1, 2, 3 or 4, wherein the group $C_{aa}H_{2aa+1}$ is unsubstituted or substituted where one or more H atoms are replaced by F atoms; or R27 and a $CH_2$ group of R25 or R26 together with the N atom to which they are bonded form a 5- or 6-membered ring; or R25 and R26 together with the N atom to which they are bonded form a 5- or 6-membered ring; or R8, R9 and R10 are independently of one another NR32COR30, NR32CSR30 or $NR32SO_2R30$; wherein R30 H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;

R32 and R33 are independently of one another H or $C_hH_{2h+1}$;
  cc is 1, 2, 3, 4, 5 or 6;
  yy is 3, 4, 5 or 6;
  h is 1, 2, 3 or 4; wherein the group $C_hH_{2h+1}$ is unsubstituted or substituted where one or more H atoms are replaced by F atoms, and wherein the groups $C_{cc}H_{2cc+1}$ and $C_{yy}H_{2yy-1}$ independently of another are unsubstituted or substituted where one or more H atoms are replaced by F atoms and/or one or more $CH_2$ groups are replaced by O or NR31;

R31 is H, $C_{kk}H_{2kk+1}$ or COR65;
  kk is 1, 2, 3, or 4, wherein the group $C_{kk}H_{2kk+1}$ is unsubstituted or substituted where one or more H atoms are replaced by F atoms, R65 is H or $C_{xx}H_{2xx+1}$;
    xx is 1, 2, 3 or 4, wherein the group $C_{xx}H_{2xx+1}$ is unsubstituted where one or more H atoms are replaced by F atoms; or R31 together with a $CH_2$ group of R30 and the N atom to which they are jointly bonded form a 5- or 6-membered ring; or R30 is a 5- or 6-membered heteroaryl chosen from pyridyl, imidazolyl, pyrazolyl, pyrrolyl, triazolyl, tetrazolyl, thienyl, thiazolyl and oxazolyl; which is unsubstituted or substituted by up to three substituents chosen from F, Cl, Br, I, $C_{oo}H_{2oo+1}$, and NR70R71, R70 and R71 are independently of one another H, $C_{uu}H_{2uu+1}$ or COR72;

R72 is H or $C_{vv}H_{2vv+1}$; oo, uu and vv are independently of one another 1, 2, 3 or 4, wherein the groups $C_{oo}H_{2oo+1}$, $C_{uu}H_{2uu+1}$ and $C_{vv}H_{2vv+1}$ independently of one another are unsubstituted or substituted where one or more H atoms are replaced by F atoms; or R8, R9 and R10 are independently of one another H, F, Cl, Br, I, $NO_2$, CN, OH, $NH_2$, $C_{ee}H_{2ee+1}$, $C_{ww}H_{2ww-1}$, $OC_{ff}H_{2ff+1}$, NR40R41, CONR40R41, COOR42, COR42 or OCOR42;
  ee and ff are independently of one another 1, 2, 3 or 4;
  ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms; R40 and R41 are independently of one another H or $C_{tt}H_{2tt+1}$;
    tt is 1, 2, 3, 4, 5, 6, 7 or 8, wherein the group $C_{tt}H_{2tt+1}$ is unsubstituted or substituted where one or more H atoms are replaced by F atoms; or R40 and R41 are independently of one another chosen from hydroxyethyl, N,N-dimethylaminoethyl, N,N-diethylaminoethyl, pyrrolidinoethyl, N-methylpiperazinoethyl, piperazinoethyl, morpholinoethyl and piperidinoethyl; or R40 and R41 together with the N atom to which they are bonded form a ring chosen from pyrrolidine, piperidine, N-methylpiperazine, piperazine and morpholine;

R42 is H or $C_{hh}H_{2hh+1}$;
  hh is 1, 2, 3 or 4, wherein the group $C_{hh}H_{2hh+1}$ is unsubstituted or substituted where one or more H atoms are replaced by F atoms;

Y is chosen from fluorine, chlorine, bromine, hydroxyl and all anionic forms of pharmacologically acceptable mono-, di- or tricarboxylic acids or sulfonic acids;

or a pharmaceutically acceptable salt thereof, or a trifluoroacetic acid salt thereof, in any stereoisomeric form, or a mixture of any such compounds in any ratio.

3. A compound as claimed in claim 1, in which R1, R2, R3 and R4 are independently of one another H, F, Cl, Br, OH, $NH_2$, $C_aH_{2a+1}$, cycloalkyl with 3, 4, 5 or 6 C atoms, or $OC_bH_{2b+1}$;

a and b are independently of one another 1, 2, 3 or 4, wherein the groups $C_aH_{2a+1}$ and $OC_bH_{2b+1}$ independently of one another are unsubstituted or substituted where one or more H atoms are replaced by F atoms; or R1, R2, R3 and R4 are independently of one another NR11R12;

R11 and R12 are independently of one another H, $C_eH_{2e+1}$ or $C_{rr}H_{2rr-1}$;

e is 1, 2, 3 or 4;

rr is 3, 4, 5 or 6, wherein the groups $C_eH_{2e+1}$ and $C_{rr}H_{2rr-1}$ independently of one another are unsubstituted or substituted where one or more H atoms are replaced by F atoms; or R11 and R12 together with the N atom to which they are bonded form a ring chosen from pyrrolidine, piperidine, N-methylpiperazine, piperazine and morpholine; or R11 and R12 are independently of one another COR14, CSR14, CONHR14, CSNHR14 or $SO_2R14$; wherein R14 is $C_gH_{2g+1}$;

g is 1, 2, 3 or 4, wherein the group $C_gH_{2g+1}$ is unsubstituted or substituted where one or more H atoms are replaced by F atoms; or R1, R2, R3 and R4 are independently of one another $OSO_3H$, $SO_3H$, or $SO_2R15$;

R15 is $C_kH_{2k+1}$ or NR17R18;

k is 1, 2, 3 or 4, wherein the group $C_kH_{2k+1}$ is unsubstituted or substituted where one or more H atoms are replaced by F atoms;

R17 and R18 are independently of one another H or $C_mH_{2m+1}$;

m is 1, 2, 3, 4 or 5, wherein the group $C_mH_{2m+1}$ is unsubstituted or substituted where one or more H atoms are replaced by F atoms; or R17 and R18 together with the N atom to which they are bonded a 5- or 6-membered ring;

with the proviso that R2 is not H;

R5 and R6 are independently of one another methyl or trifluoromethyl;

R7 is H;

R8, R9 and R10 are independently of one another $OSO_3H$, $SO_3H$ or $SO_2R23$; wherein R23 is $C_{nn}H_{2nn+1}$ or NR25R26;

nn is 1, 2, 3, 4 or 5, wherein the group $C_{nn}H_{2nn+1}$ is unsubstituted or substituted where one or more H atoms are replaced by F atoms;

R25 and R26 are independently of one another H, CN, $C_zH_{2z+1}$, or $C_zH_{2z+1}$ in which a first $CH_2$ group bonded to the nitrogen of NR25R26 is replaced by CO or OS and a second $CH_2$ is replaced by NR27;

z is 1, 2, 3, 4, 5 or 6, wherein the group $C_zH_{2z+1}$ is unsubstituted or substituted where one or more H atoms are replaced by F atoms;

R27 is H or $C_{aa}H_{2aa+1}$;

aa is 1, 2, 3 or 4, wherein the group $C_{aa}H_{2aa+1}$ is unsubstituted or substituted where one or more H atoms are replaced by F atoms; or R27 and a $CH_2$ group of R25 or R26 together with the N atom to which they are bonded a 5- or 6-membered ring; or R25 and R26 together with the N atom to which they are bonded form a 5- or 6-membered ring, or R8, R9 and R10 are independently of one another NR32COR30, NR32CSR30 or $NR32SO_2R30$; wherein R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a $CH_2$ group is replaced by O or NR33;

R32 and R33 are H, methyl or $CF_3$;

cc is 1, 2, 3, 4, 5 or 6;

yy is 3, 4, 5 or 6, wherein the groups $C_{cc}H_{2cc+1}$ and $C_{yy}H_{2yy-1}$ independently of one another are unsubstituted or substituted where one ore more H atoms are replaced by F atoms and/or one or more $CH_2$ groups are replaced by O or NR31;

R31 is H, methyl, ethyl, $CF_3$, $CH_2CF_3$, acetyl or propionyl; or

R31 together with a $CH_2$ group of R30 and the N atom to which they are jointly bonded form a 5- or 6-membered ring; or R30 is pyridyl, imidazolyl, pyrazolyl, triazolyl, tetrazolyl, thiazolyl or oxazolyl, which are unsubstituted or substituted by up to 3 substituents chosen from F, Cl, methyl, ethyl, trifluoromethyl, $NH_2$, and NHacetyl; or R8, R9 and R10 are independently of one another H, F, Cl, OH, $NH_2$, $C_{ee}H_{2ee+1}$, $C_{ww}H_{2ww-1}$, $OC_{ff}H_{2ff+1}$, NR40R41, CONR40R41, COOR42 or OCOR42, ee and ff are independently of one another 1, 2, 3 or 4;

ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms are replaced by F atoms; R40 and R41 are H or $C_{tt}H_{2tt+1}$;

tt is 1, 2, 3 or 4, wherein the group $C_{tt}H_{2tt+1}$ is unsubstituted or substituted where one or more H atoms are replaced by F atoms; or R40 and R41 independently of one another are hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or R40 and R41 together with the N atom to which they are bonded form a pyrrolidine, piperidine, N-methylpiperazine, piperazine or morpholine ring;

R42 is H or $C_{hh}H_{2hh+1}$;

hh is 1, 2, 3 or 4, wherein the $C_{hh}H_{2hh+1}$ is unsubstituted or substituted where one or more H atoms are replaced by F atoms;

Y is chosen from fluorine, chlorine, bromine, hydroxyl and all anionic forms of pharmacologically acceptable mono-, di- or tricarboxylic acids and sulfonic acids;

or a pharmaceutically acceptable salt thereof, or a trifluoroacetic acid salt thereof, in any stereoisomeric form, or a mixture of any such compounds in any ratio.

4. A compound as claimed in claim 1, in which R1 and R3 is H;

R2 and R4 are independently of one another H, F, Cl, Br, OH, $NH_2$, $C_aH_{2a+1}$, cycloalkyl with 3, 4, 5 or 6 C atoms, or $OC_bH_{2b+1}$; wherein a and b are independently of one another 1, 2, 3 or 4, wherein the groups $C_aH_{2a+1}$ and $OC_bH_{2b+1}$ independently of one another are unsubstituted or substituted where one or more H atoms to be replaced by F atoms;

or R2 and R4 are independently of one another NR11R12; wherein

R11 and R12 are independently of one another H or $C_eH_{2e+1}$, e is 1, 2, 3 or 4, wherein the group $C_eH_{2e+1}$ is unsubstituted or substituted where one or more H atoms to be replaced by F atoms; or R11 and R12 together with the N atom to which they are bonded form a ring chosen from pyrrolidine, piperidine, N-methylpiperazine, piperazine and morpholine; or R11 and R12 are independently of one another COR14, CSR14, CONHR14, CSNHR14 or SO$_2$R14;

R14 is $C_gH_{2g+1}$;

g is 1, 2, 3 or 4, wherein the group $C_gH_{2g+1}$ is unsubstituted or substituted where one or more H atoms to be replaced by F atoms; or R2 and R4 are independently of one another OSO$_3$H, SO$_3$H, or SO$_2$R15; wherein R15 is $C_kH_{2k+1}$ or NR17R18;

k is 1, 2, 3 or 4, wherein the group $C_kH_{2k+1}$ is unsubstituted or substituted where one or more H atoms to be replaced by F atoms;

R17 and R18 are independently of one another H or $C_mH_{2m+1}$;

m is 1, 2, 3, 4 or 5, wherein the group $C_mH_{2m+1}$ is unsubstituted or substituted where one or more H atoms to be replaced by F atoms; or R17 and R18 together with the N atom to which they are bonded form a 5- or 6-membered ring;

with the proviso that R2 is not H;

R5 and R6 are independently of one another methyl or trifluoromethyl;

R7 is H;

R8, R9 and R10 are independently of one another OSO$_3$H, SO$_3$H or SO$_2$R23; wherein R23 is $C_{nn}H_{2nn+1}$ or NR25R26;

nn is 1, 2, 3, 4 or 5, wherein the group $C_{nn}H_{2nn+1}$ is unsubstituted or substituted where one or more H atoms to be replaced by F atoms;

R25 and R26 are independently of one another H, CN, $C_zH_{2z+1}$, or $C_zH_{2z+1}$ in which a first CH$_2$ group bonded to the nitrogen of NR25R26 is replaced by CO or CS and a second CH$_2$ is replaced by NR27;

z is 1, 2, 3, 4, 5 or 6, wherein the group $C_zH_{2z+1}$ is unsubstituted or substituted where one or more H atoms to be replaced by F atoms;

R27 is H or $C_{aa}H_{2aa+1}$;

aa is 1, 2, 3 or 4, wherein the group $C_{aa}H_{2aa+1}$ is unsubstituted or substituted where one or more H atoms to be replaced by F atoms or R27 and a CH$_2$ group of R25 or R26 together with the N atom to which they are bonded form a 5- or 6-membered ring; or R25 and R26 together with the N atom to which they are bonded form a 5- or 6-membered ring, or R8, R9 and R10 are independently of one another NR32COR30, NR32CSR30 or NR32SO$_2$R30;

R30 is H, OH, $C_{cc}H_{2cc+1}$, $C_{yy}H_{2yy-1}$, pyrrolidinyl or piperidinyl, wherein the pyrrolidinyl or piperidinyl is unsubstituted or substituted where a CH$_2$ group is replaced by O or NR33;

R32 and R33 are independently of one another H, methyl or CF$_3$;

cc is 1, 2, 3, 4, 5 or 6;

yy is 3, 4, 5 or 6, wherein the groups $C_{cc}H_{2cc+1}$ and independently of one another are unsubstituted or substituted where one or more H atoms are replaced by F atoms and/or one or more CH$_2$ groups are replaced by O or NR31;

R31 is H, methyl, ethyl, CF$_3$, CH$_2$CF$_3$, acetyl or propionyl; or

R31 together with a CH$_2$ group of R30 and the N atom to which they are jointly bonded form a 5- or 6-membered ring; or R30 is pyridyl, imidazolyl, pyrazolyl, triazolyl, tetrazolyl, thiazolyl or oxazolyl, which are unsubstituted or substituted by up to 3 substituents chosen from F, Cl, methyl, ethyl, trifluoromethyl, NH$_2$, and NHacetyl; or R8, R9 and R10 are independently of one another H, F, Cl, OH, NH$_2$, $C_{ee}H_{2ee+1}$, $C_{ww}H_{2ww-1}$, $OC_{ff}H_{2ff+1}$, NR40R41, CONR40R41, COOR42 or OCOR42, ee and ff are independently of one another 1, 2, 3 or 4;

ww is 3, 4, 5 or 6, wherein the groups $C_{ee}H_{2ee+1}$, $C_{ww}H_{2ww-1}$ and $OC_{ff}H_{2ff+1}$ independently of one another are unsubstituted or substituted where one or more H atoms to be replaced by F atoms;

R40 and R41 is H or $C_{tt}H_{2tt+1}$;

tt is 1, 2, 3 or 4, wherein the group $C_{tt}H_{2tt+1}$ is unsubstituted or substituted where one or more H atoms to be replaced by F atoms; or R40 and R41 are independently of one another hydroxyethyl, N,N-dimethylaminoethyl, N,N-diethylaminoethyl, pyrrolidinoethyl, N-methylpiperazinoethyl, piperazinoethyl, morpholinoethyl or piperidinoethyl; or R40 and R41 together with the N atom to which they are bonded form a pyrrolidine, piperidine, N-methylpiperazine, piperazine or morpholine ring;

R42 is H or $C_{hh}H_{2hh+1}$; hh is 1, 2, 3 or 4, wherein the group $C_{hh}H_{2hh+1}$ is unsubstituted or substituted where one or more H atoms to be replaced by F atoms;

Y is chosen from fluorine, chlorine, bromine, hydroxyl and all anionic forms of pharmacologically acceptable mono-, di- or tricarboxylic acids and sulfonic acids;

or a pharmaceutically acceptable salt thereof, or a trifluoroacetic acid salt thereof, in any stereoisomeric form, or a mixture of any such compounds in any ratio.

5. A compound as claimed in claim 1, chosen from:
a. 6,8-dichloro-2,2-dimethyl-4-phenyl-1,2,3,4-tetrahydroisoquinolinium trifluoroacetate;
b. 6,8-dichloro-2,2-dimethyl-4-(4-sulfamoylphenyl)-1,2,3,4-tetrahydroisoquinolinium trifluoroacetate;
c. 4-(4-acetylaminophenyl)-6,8-dichloro-2,2-dimethyl-1,2,3,4-tetrahydroisoquinolinium iodide;
d. (+)-4-(4-acetylaminophenyl)-6,8-dichloro-2,2-dimethyl-1,2,3,4-tetrahydroisoquinolinium iodide;
e. (−)-4-(4-acetylaminophenyl)-6,8-dichloro-2,2-dimethyl-1,2,3,4-tetrahydroisoquinolinium iodide;
f. (+)-4-(4-acetylaminophenyl)-6,8-dichloro-2,2-dimethyl-1,2,3,4-tetrahydroisoquinolinium chloride;
g. 4-(4-aminophenyl)-6,8-dichloro-2,2-dimethyl-1,2,3,4-tetrahydroisoquinolinium chloride; hydrochloride;
h. 6,8-dichloro-4-[4-(3-ethylureido)phenyl]-2,2-dimethyl-1,2,3,4-tetrahydroisoquinolinium chloride;

or a pharmaceutically acceptable salt thereof, or a trifluoroacetic acid salt thereof, in any stereoisomeric form, or a mixture of any such compounds in any ratio.

6. A method for the treatment of disorders which can be influenced by inhibition of the sodium-proton exchanger of subtype III (NHE3) comprising, administering to a patient in need thereof at least one compound as claimed in claim 1, with the proviso that said compound is not a trifluoroacetic acid salt.

7. A method for the treatment of disorders of respiratory drive comprising, administering to a patient in need thereof at least one compound as claimed in claim 1, with the proviso that said compound is not a trifluoroacetic acid salt.

8. A method for the treatment of disorders of respiratory drive of claim 7, wherein the disorders of respiratory drive are sleep-related respiratory disorders.

9. A method for the treatment of disorders of respiratory drive of claim 8, wherein the sleep-related respiratory disorders are sleep apneas.

10. A method for the treatment of snoring comprising, administering to a patient in need thereof at least one compound as claimed in claim 1, with the proviso that said compound is not a trifluoroacetic acid salt.

11. A method for the treatment of acute and chronic renal disorders comprising, administering to a patient in need thereof at least one compound as claimed in claim 1, with the proviso that said compound is not a trifluoroacetic acid salt.

12. A method for the treatment of acute and chronic renal disorders of claim 11, wherein the acute and chronic renal disorders are acute renal failure and of chronic renal failure.

13. A method for the treatment of disorders of intestinal function comprising, administering to a patient in need thereof at least one compound as claimed in claim 1, with the proviso that said compound is not a trifluoroacetic acid salt.

14. A method for the treatment of disorders of biliary function comprising, administering to a patient in need thereof at least one compound as claimed in claim 1, with the proviso that said compound is not a trifluoroacetic acid salt.

15. A method for the treatment of disorders of ischemic states of the peripheral and central nervous system and of stroke comprising, administering to a patient in need thereof at least one compound as claimed in claim 1, with the proviso that said compound is not a trifluoroacetic acid salt.

16. A method for the treatment of disorders of ischemic states of the peripheral organs and limbs comprising, administering to a patient in need thereof at least one compound as claimed in claim 1, with the proviso that said compound is not a trifluoroacetic acid salt.

17. A method for the treatment of states of shock comprising, administering to a patient in need thereof at least one compound as claimed in claim 1, with the proviso that said compound is not a trifluoroacetic acid salt.

18. A method for preserving and storing transplants for surgical interventions comprising, contacting the transplant with at least one compound as claimed in claim 1, with the proviso that said compound is not a trifluoroacetic acid salt.

19. A method of protecting a transplant organ in a host, comprising administering to the host in need thereof at least one compound as claimed in claim 1,
wherein the host is a transplant donor or a transplant recipient, with the proviso that said compound is not a trifluoroacetic acid salt.

20. A method for the treatment of diseases in which cell proliferation is a primary or secondary cause comprising, administering to a patient in need thereof at least one compound as claimed in claim 1, with the proviso that said compound is not a trifluoroacetic acid salt.

21. A method for the treatment of disorders of lipid metabolism comprising, administering to a patient in need thereof at least one compound as claimed in claim 1, with the proviso that said compound is not a trifluoroacetic acid salt.

22. A method for the treatment of infection by ectoparasites comprising, administering to a patient in need thereof at least one compound as claimed in claim 1, with the proviso that said compound is not a trifluoroacetic acid salt.

23. A pharmaceutical comprising at least one compound as claimed in claim 1 and at least one pharmaceutical carrier, with the proviso that said compound is not a trifluoroacetic acid salt.

* * * * *

UNITED STATES PATENT AND TRADEMARK OFFICE
CERTIFICATE OF CORRECTION

PATENT NO. : 6,703,405 B2
DATED : March 9, 2004
INVENTOR(S) : Armin Hofmeister et al.

It is certified that error appears in the above-identified patent and that said Letters Patent is hereby corrected as shown below:

Column 28,
Lines 12 and 15, "unsubsitituted" should read -- unsubstituted --.

Column 29,
Line 61, after "COR72", insert -- ; --.

Column 30,
Line 52, "CONR11 R12" should read -- CONR11R12 --.

Column 31,
Line 2, "CCNHR14," should read -- CONHR14, --.
Line 45, "$C_{nn}H_{2nn-1}$," should read -- $C_{nn}H_{2nn+1}$, --.
Line 54, "OS" should read -- CS --.
Line 55, "$O_zH_{2z+1}$" should read -- $C_zH_{2z+1}$ --.

Column 33,
Line 63, "OS" should read -- CS --.

Column 34,
Line 20, "one ore more" should read -- one or more --.

Column 36,
Line 6, after "$C_{cc}H_{2cc+1}$ and", insert -- $C_{yy}H_{2yy-1}$ --.
Line 18, "Cl ," should read -- Cl, --.

Signed and Sealed this

Thirty-first Day of May, 2005

JON W. DUDAS
*Director of the United States Patent and Trademark Office*